US011920930B2

(12) United States Patent
Adie et al.

(10) Patent No.: US 11,920,930 B2
(45) Date of Patent: Mar. 5, 2024

(54) LIGHT-SHEET PHOTONIC-FORCE OPTICAL COHERENCE ELASTOGRAPHY

(71) Applicant: Cornell University, Ithaca, NY (US)

(72) Inventors: Steven G Adie, Ithaca, NY (US); Yuechuan Lin, Ithaca, NY (US); Nichaluk Leartprapun, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/759,851

(22) PCT Filed: Feb. 1, 2021

(86) PCT No.: PCT/US2021/016110
§ 371 (c)(1),
(2) Date: Jul. 29, 2022

(87) PCT Pub. No.: WO2021/155382
PCT Pub. Date: Aug. 5, 2021

(65) Prior Publication Data
US 2023/0072425 A1 Mar. 9, 2023

Related U.S. Application Data

(60) Provisional application No. 62/968,961, filed on Jan. 31, 2020.

(51) Int. Cl.
*G01B 9/02* (2022.01)
*G01B 9/02001* (2022.01)
(Continued)

(52) U.S. Cl.
CPC ..... *G01B 9/02091* (2013.01); *G01B 9/02007* (2013.01); *G01B 9/02012* (2013.01);
(Continued)

(58) Field of Classification Search
CPC ............ G01B 9/02091; G01B 9/02007; G01B 9/02012; G01B 9/02034; G01B 9/02029;
(Continued)

(56) References Cited

U.S. PATENT DOCUMENTS

2007/0078348 A1 4/2007 Holman
2016/0078309 A1* 3/2016 Feldman ............... G06T 7/0012
382/131
(Continued)

OTHER PUBLICATIONS

International Search Report and Written Opinion for PCT/US2021/016110, dated Apr. 14, 2021, 15 pages.

*Primary Examiner* — Uzma Alam
*Assistant Examiner* — Jonathon Cook
(74) *Attorney, Agent, or Firm* — COZEN O'CONNOR

(57) ABSTRACT

Disclosed are devices and techniques based on optical coherence tomography (OCT) technology in combination with optical actuation. A system for providing optical actuation and optical sensing can include an optical coherence tomography (OCT) device that performs optical imaging of a sample based on optical interferometry from an optical sampling beam interacting with an optical sample and an optical reference beam; an OCT light source to provide an OCT imaging beam into the OCT device which splits the OCT imaging beam into the optical sampling beam and the optical reference beam; and a light source that produces an optical actuation beam that is coupled along with the optical sampling beam to be directed to the sample to actuate particles or structures in the sample so that the optical imaging captures information of the sample under the optical actuation.

26 Claims, 14 Drawing Sheets

(51) Int. Cl.
*G01B 9/02091* (2022.01)
*G01N 21/17* (2006.01)
*G01N 21/64* (2006.01)
*A61B 5/00* (2006.01)

(52) U.S. Cl.
CPC ......... *G01B 9/02034* (2013.01); *G01N 21/17* (2013.01); *G01N 21/6486* (2013.01); *A61B 5/0066* (2013.01); *G01N 2021/1787* (2013.01)

(58) Field of Classification Search
CPC .... G01N 21/17; G01N 21/64; G01N 21/6486; G01N 2021/1787; A61B 5/0066; A61B 3/102

See application file for complete search history.

(56) References Cited

U.S. PATENT DOCUMENTS

| | | | |
|---|---|---|---|
| 2016/0327779 | A1 | 11/2016 | Hillman |
| 2016/0341539 | A1 | 11/2016 | Adie et al. |
| 2017/0241765 | A1* | 8/2017 | Adie ................. G01B 9/02002 |
| 2018/0164277 | A1 | 6/2018 | Watanabe et al. |
| 2018/0214023 | A1* | 8/2018 | Chen ...................... A61B 8/485 |
| 2019/0250388 | A1 | 8/2019 | Hillman et al. |
| 2019/0335992 | A1* | 11/2019 | Kataoka ............... A61B 3/0008 |
| 2020/0201058 | A1* | 6/2020 | Ginner ............... G01N 15/1436 |

* cited by examiner

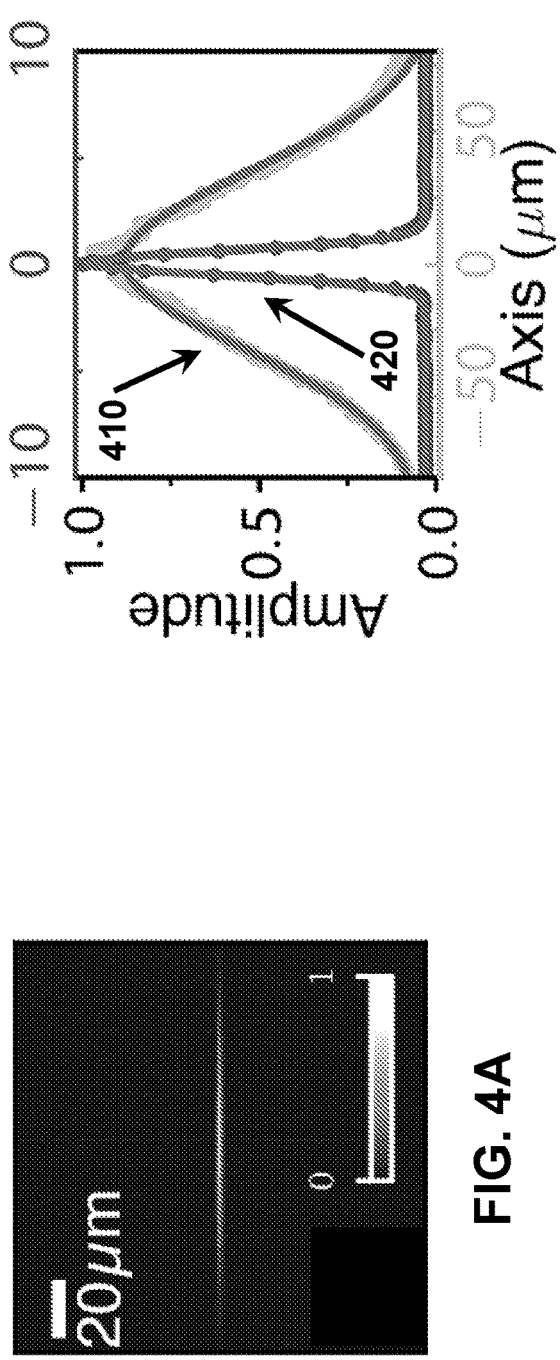
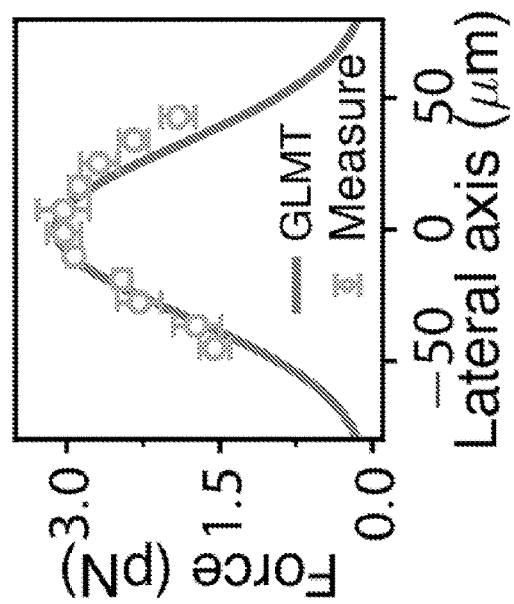
FIG. 4A
FIG. 4B
FIG. 4C

LIGHT-SHEET PHOTONIC-FORCE OPTICAL COHERENCE ELASTOGRAPHY

CROSS-REFERENCE TO RELATED APPLICATION

This patent document claims priority to U.S. Provisional Application No. 62/968,961, filed on Jan. 31, 2020, entitled "LIGHT-SHEET PHOTONIC-FORCE OPTICAL COHERENCE ELASTOGRAPHY BASED ON OPTICAL COHERENCE TOMOGRAPHY", the disclosure of which is hereby incorporated by reference herein in its entirety.

STATEMENT OF GOVERNMENT SUPPORT

This patent document is a 371 National Phase Application of PCT Application No. PCT/US2021/016110, entitled "LIGHT-SHEET PHOTONIC-FORCE OPTICAL COHERENCE ELASTOGRAPHY" filed on Feb. 1, 2021, which claims priority to U.S. Provisional Application No. 62/968, 961, entitled "LIGHT-SHEET PHOTONIC-FORCE OPTICAL COHERENCE ELASTOGRAPHY BASED ON OPTICAL COHERENCE TOMOGRAPHY" and filed on Jan. 31, 2020The entire content of the before-mentioned patent application is incorporated by reference herein in its entirety as part of the disclosure of this document.

TECHNICAL FIELD

This patent document relates to optical sensing or detection based on optical coherence tomography (OCT).

BACKGROUND

Optical sensing based on light can be used in various applications due to various features offered by interactions of light and matter, including the less invasive to a target sample of using light to probe or interact with the sample. Optical coherence tomography (OCT) is one of examples of optical sensing technologies for various applications including imaging tissues, chemical materials or biological materials.

SUMMARY

This patent document discloses devices, techniques and applications based on optical sensing or detection of a sample using optical coherence tomography (OCT) while applying a separate modulated light beam to the sample to cause an optical or photonic force onto the sample to agitate part of the sample so the OCT measurements performed on the agitated part of the sample can be processed to characterize certain properties of the sample. In various implementations, the disclosed technology can be implemented to provide a system for providing optical actuation and optical sensing and includes an optical coherence tomography (OCT) device that performs optical imaging of a sample based on optical interferometry from an optical sampling beam interacting with a sample and an optical reference beam; an OCT light source to provide an OCT imaging beam into the OCT device which splits the OCT imaging beam into the optical sampling beam and the optical reference beam; and a light source that produces an optical actuation beam that is coupled along with the optical sampling beam to be directed to the sample to actuate particles, or any other optically scattering structures, in the sample so that the optical imaging captures information of the sample under the optical actuation. The optical actuation beam is in form of a light-sheet that optically interacts with a region of the sample at the same time. In some implementations, a sampling beam control device (e.g., a beam scanner) can be provided to control the optical sampling beam independently from the optical actuation beam in form of the light-sheet. This use of separate light to cause mechanical actuation in the sample is advantageous in that there is no physical contact with the sample and thus avoids various technical issues in mechanical actuation by contact of a mechanical or acoustic wave actuator or other contact-type actuators. The disclosed devices and techniques may be applied to various optical sensing applications including improving measurements in optical coherence elastography (OCE). In some implementations, fluorescence imaging can be further performed at the same time with the photonic-force assisted OCE to obtain further information of the sample via the fluorescence imaging.

In one example, the disclosed technology can be used to provide system for providing optical actuation and optical sensing to include an optical coherence tomography (OCT) device that performs optical imaging of a sample based on optical interferometry from an optical sampling beam interacting with an optical sample and an optical reference beam; an OCT light source to provide an OCT imaging beam into the OCT device which splits the OCT imaging beam into the optical sampling beam and the optical reference beam; a light source that produces an optical actuation beam that is coupled along with the optical sampling beam to be directed to the sample to actuate particles or structures in the sample so that the optical imaging captures information of the sample under the optical actuation; and an optical beam shaping module located in an optical path between the photonic-force light source and the sample to shape the optical actuation beam into a light-sheet to illuminate a region of the sample. The light-sheet beam can be defined as any form of a light beam (e.g., a laser beam) which is extended along one or multiple axes of the beam to illuminate a sample over an extended area or volume of the sample simultaneously, rather than creating a point-like sample illumination.

In another example, the disclosed technology can be implemented to provide a method of quantifying three-dimensional mechanical properties of a sample at microscale. This method includes operating a first light source emitting light in a first optical band of optical wavelengths to produce a sampling beam optically interacting with the sample and a reference beam, operating a phase-sensitive low-coherence optical interferometry device to obtain optical images of the sample from optical interference of the sampling beam and the reference beam, operating a second light source to produce an optical actuation beam at a second optical wavelength different from the wavelengths in the first band, operating an optical beam shaping module located in an optical path between the second light source and the sample to shape the optical actuation beam into a light sheet, directing the optical actuation beam shaped into the light-sheet to the sample to actuate mechanical movements of microparticle probes so that the optical images capture first information of the mechanical movements of the microparticle probes, and using the first information to obtain second information of the mechanical properties of the sample.

In another example, the disclosed technology can be implemented to provide a system for quantifying three-dimensional mechanical properties of a sample at microscale. This system includes a first light source configured to emit light in a first optical band of optical wavelengths to produce a sampling beam optically interacting with the sample and a reference beam, a phase-sensitive low-coherence optical interferometry device configured to obtain optical images of the sample from optical interference of the sampling beam and the reference beam, a second light source configured to produce an optical actuation beam in form of a light-sheet at a second optical wavelength different from the wavelengths in the first band, wherein the optical actuation beam actuates mechanical movements of microparticle probes so that the optical images capture first information of the mechanical movements of the microparticle probes, and a processor configured to use the first information to obtain second information of the mechanical properties of the sample.

In another example, the disclosed technology can be implemented to provide a system for quantifying three-dimensional mechanical properties of a sample at microscale. This system includes a first light source configured to emit light in a first optical spectral band of optical wavelengths to produce a sampling beam optically interacting with the sample and a reference beam, a phase-sensitive low-coherence optical interferometry device configured to obtain optical images of the sample from optical interference of the sampling beam and the reference beam, a second light source configured to produce an optical actuation beam in form of a sheet at a second optical wavelength different from the wavelengths in the first optical spectral band, wherein the optical actuation beam actuates mechanical movements of microparticle probes so that the optical images capture first information of the mechanical movements of the microparticle probes, a processor configured to use the first information to obtain second information of the mechanical properties of the sample. A third light source that produces one or multiple fluorescent excitation lights to the sample to cause the sample to emit fluorescent light, and a fluorescent detection module located to receive the emitted fluorescent light from the sample to measure one or more properties of the sample from the emitted fluorescent light.

In yet another example, the disclosed technology can be implemented to provide a method of quantifying a mechanical property of a sample at micro-scale. This method includes operating a first light source emitting light in a first optical band of optical wavelengths to produce a sampling beam optically interacting with the sample and a reference beam, operating an optical interferometry device to obtain optical images of the sample from optical interference of the sampling beam and the reference beam, operating a second light source to produce an optical actuation beam at a second optical wavelength different from the wavelengths in the first band, operating an optical beam shaping module located in an optical path between the second light source and the sample to shape the optical actuation beam into a light sheet, directing the optical actuation beam shaped into the light-sheet to the sample to actuate mechanical movements of microparticle probes in the sample so that the optical images capture first information of the mechanical movements of the microparticle probes corresponding to a first condition of the sample, changing the first condition of the sample into a second condition of the sample, directing the optical actuation beam shaped into the light-sheet to the sample to actuate mechanical movements of the microparticle probes in the sample so that the optical images capture second information of the mechanical movements of the microparticle probes corresponding to the second condition of the sample, using the first information corresponding to the first condition of the sample to obtain information of the mechanical property of the sample corresponding to the first condition of the sample, and using the second information corresponding to the second condition of the sample to obtain information of the mechanical property of the sample corresponding to the second condition of the sample.

Those and other aspects of the disclosed devices and techniques and their implementations and applications are described in greater detail in the drawings, the description and the claims.

BRIEF DESCRIPTION OF THE DRAWINGS

FIG. 4A shows an example of a measured cross-section of a light-sheet beam.

FIG. 4B shows an example of a measured amplitude profile of a light-sheet beam.

FIG. 4C shows an example of a measured force profile along a long axis of an optical actuation light sheet.

DETAILED DESCRIPTION

Figure 1:
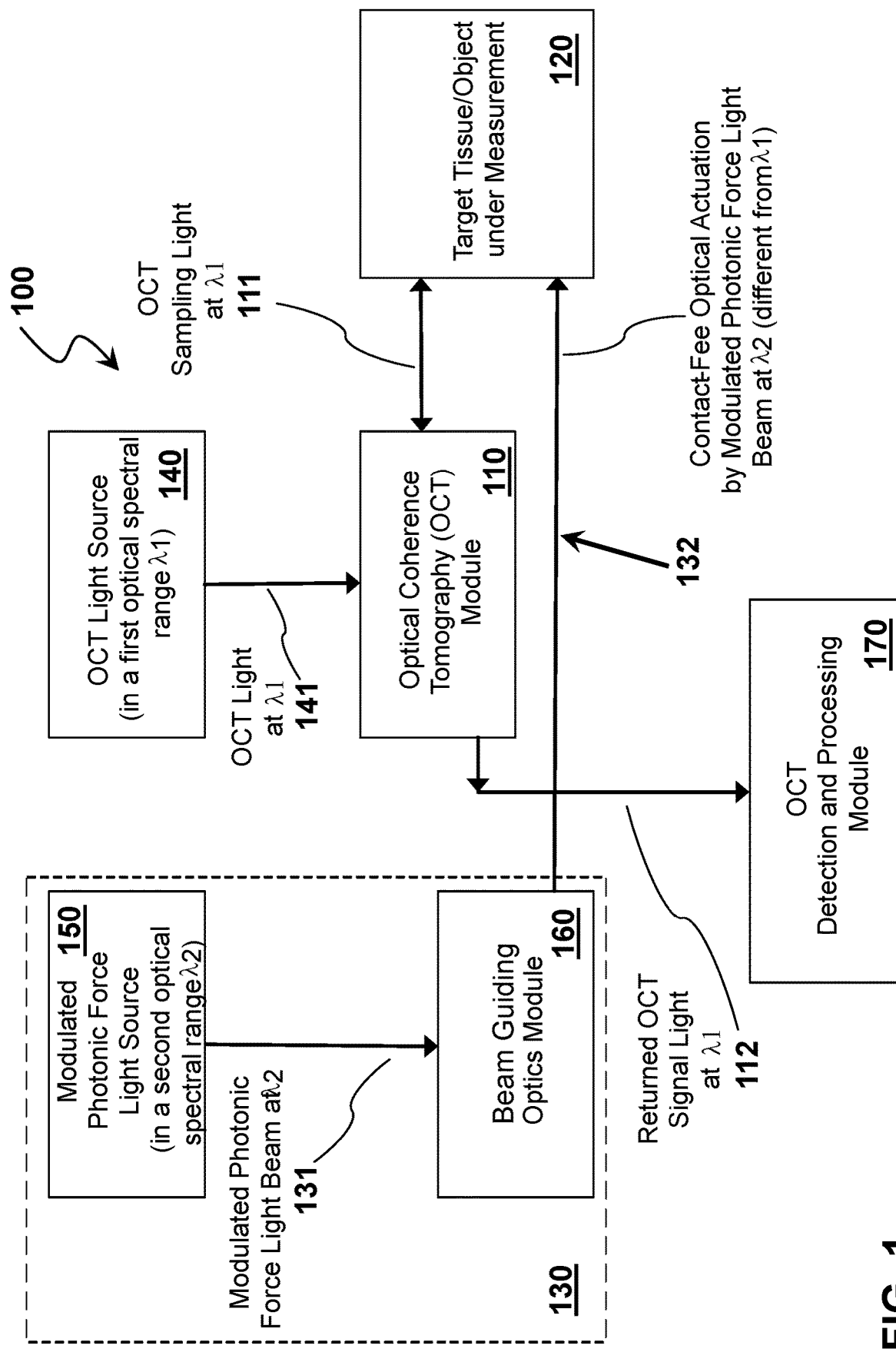
FIG. 1 shows an example of an implementation of a photonic-force assisted optical coherence elastography (OCE) system based on optical actuation of the sample according to the disclosed technology.

Tissue measurements based on elastography use quantitative imaging of the mechanical response of a target tissue and allow a clinical professional (or a biomedical scientist) to use an elastography system as a tool to diagnose diseases that alter mechanical properties of tissues, or for exploring how biological processes are influenced by tissue mechanics. The dynamic range of Young's modulus varies by over two orders of magnitude among different types of healthy and diseased tissue and the quantification of biomechanical properties during disease progression by precision elastography measurements could lead to earlier diagnosis and improved treatment. In elastography, the mechanical response of a tissue sample is imaged by mechanically loading the sample and measuring the resulting (spatially-localized) displacements. Based on the intuition afforded by palpation, "soft" tissue regions will compress (or "strain") more than "stiff" regions. Optical coherence tomography (OCT) can be used as an effective imaging modality to quantify tissue displacements and the OCT measurements contain the mechanical loading characteristics, and impact the overall capabilities for imaging tissue biomechanics.

This patent document discloses, among others, optical coherence elastography devices and techniques that use an optical coherence tomography (OCT) system (1) to use a first OCT light source coupled to the OCT system to send an OCT optical imaging beam into the OCT system to perform optical imaging of a sample that is optically activated by an optical actuation beam, and (2) to use a separate second light source coupled to the OCT system to provide the optical actuation beam to the sample to exert an optical force to the sample to move particles and/or any other optically scattering structures within the sample in response to the applied optical force. The disclosed photonic-force assisted optical coherence elastography (OCE) designs and techniques may be further integrated with fluorescence imaging to simultaneously obtain the OCE measurements and the fluorescence imaging measurements.

Various aspects of the disclosed OCT technology based on the optical actuation of the sample can be implemented to provide various advantages. For example, different from some optical coherence elastography (OCE) systems where an OCT module is used for performing elastography measurements by using air puff, acoustic vibrations or other ways of mechanical actuation of the sample to cause sample displacements, the technology disclosed in this patent document includes non-contact or contact-free highly localized optical actuation by a separate optical actuation beam that is directed to an area of the sample under illumination by the OCT sampling beam to perform optical coherence elastography (OCE) measurements. The combination of the OCT and the optical actuation provides an all-optical system for efficient and three-dimensional OCE measurements and is a less invasive way of performing OCE measurements. Various techniques can be used to provide highly sensitive OCE measurements by separating signal contributions from other effects such as thermal effects caused by local heating by the optical actuation beam. The phase-sensitive nature of the OCT can be used to improve the signal to noise ratio in OCE measurements.

Additional details related to optical sensing based on measurements of displacements induced by optical scattering forces in viscoelastic media using phase-sensitive optical coherence tomography are described in the U.S. Pat. No. 10,072,920 (based on U.S. application Ser. No. 15/162,608) entitled "OPTICAL SENSING BASED ON MEASUREMENTS OF DISPLACEMENTS INDUCED BY OPTICAL SCATTERING FORCES IN VISCOELASTIC MEDIA USING PHASE-SENSITIVE OPTICAL COHERENCE TOMOGRAPHY" which is incorporated herein by reference in its entirety as part of the disclosure of this patent document.

FIG. 1 shows an example of an implementation of an OCE system based on optical actuation of the sample according to the disclosed technology. This system 100 includes two optical submodules that are integrated with each other: (1) an OCT optical module 110 to direct an OCT sampling beam 111 (in a spectral range represented by $\lambda 1$) to a target sample 120 for OCT imaging to interact with the sample and to acquire sample information based on optical interferometry, and (2) an optical actuation module 130 that performs optical actuation by using a separate optical actuation beam 132 that is in a different spectral range represented by $\lambda 2$ and is directed to an area of the sample 120 under illumination by the OCT sampling beam 111 at $\lambda 1$. In this example, two separate light sources 140 and 150 can be used to provide the OCT light at $\lambda 1$ and optical actuation light at $\lambda 2$, respectively. The optical actuation beam 131 at $\lambda 2$ produced by the light source 150 can be modulated in a suitable way (e.g., in intensity or power) to facilitate the OCE measurements. A beam guiding optics module 160 can be used to direct the modulated optical actuation beam 131 to the target sample such as, e.g., a tissue area of a patient or a part of a cell culture and is configured to produce a modulated optical actuation beam 132 in a form of a light-sheet using the beam 131 (which can be, e.g., a Gaussian beam) such that the beam 132 covers a whole extended region of the sample 120 rather than a small spot of the sample 120. In some implementations, the beam guiding optics module 160 can switch between generating a light-sheet beam (e.g., the beam 132) and a Gaussian beam (e.g., the beam 131) at its output for application to the sample. The latter can be done by, e.g., letting the Gaussian beam 131 pass through the guiding optics module 160. The returned OCT signal light 112 at $\lambda 1$ can be extracted from the OCT module 110 to be detected and processed in an OCT detection and processing module 170 to generate the desired output representing the OCE data of the target sample.

In implementations, the OCT module 110 can be in different configurations where the OCT light from the OCT light source 140 is provided as an OCT imaging beam 141 into the OCT module 110 which splits the OCT imaging beam 141 into the optical sampling beam 111 and an optical reference beam 113 (not shown in FIG. 1). The sampling beam 111 and the reference beam 113 may be spatially separated or may partially overlap in their optical paths depending on the specific OCT configurations. Various OCT systems or configurations may be used to implement the disclosed OCT imaging and optical actuation by using the first and second light sources 140 and 150, respectively. As an example, one of OCT system configurations uses two separate optical arms to form an optical interference between the light from the two optical arms where the light from a suitable OCT light source for OCT imaging (i.e., the first light source 140) is split into a reference beam and a sampling beam which propagate in two separate optical paths, the optical reference arm and the optical sampling arm, respectively. The light source 140 may be partially coherent or low-coherence light source to provide a broadband input light for OCT imaging based on broadband interferometry. The sampling beam is directed along the optical sampling arm to impinge on the sample under study, while the reference beam is directed in a separate path in the optical reference arm towards a reference surface. The sampling beam reflected from the sample and the reference beam reflected from the reference surface are then brought to spatially overlap with each other to optically interfere and the interference fringes or pattern of this interference can be used to obtain imaging information of the sample. A beam splitter may be used to split the light from the OCT light source and to combine the reflected sampling beam and the reflected reference beam for detection at an optical detector.

In some implementations, for optical actuation of the sample, an optical actuation beam produced by the second light source 150 can be coupled to the optical sampling arm of the OCT system to direct the optical actuation beam to the sample to exert an optical force to the sample to move the particles or any other optically scattering structures within the sample in response to the applied optical force. In other implementations, the optical actuation beam can follow an optical path to the sample that is separate from the optical path of the sampling beam generated by the OCT system. The system 100 can also provide shaping of the optical actuation beam (which can be done, e.g., using the guiding optics module 160, as discussed above) that is either independent from or correlated with the shaping of the OCT sampling beam (which can be performed, for example, by the OCT module 110). In some implementations, optical scattering forces are exerted by the (modulated) optical actuation beam to induce localized vibrations, e.g., on the order of sub-nano to nano-meters in the sample (e.g., viscoelastic gelatin or silicone phantoms or bovine liver). Detection of the induced vibrations via phase-sensitive OCT can be used to provide a novel approach for 3D cellular-resolution elastography.

In applications, the disclosed technology can be implemented to construct an all-optical mechanical imaging system, including a light-sheet photonic force (PF) excitation and phase-sensitive low-coherence optical interferometry for high throughput detecting and quantifying three-dimensional mechanical properties of viscoelastic materials in situ and in vivo in a non-destructive manner. In specific implementations, the light-sheet photonic force beam may be a weakly-focused or collimated laser beam with an extended illumination area to apply a desired photonic force, originating from radiation pressure of laser beam, simultaneously exerted on a number of microparticles (and/or nanoparticles) contained in or embedded into viscoelastic materials. An optical power modulated or intensity modulated light-sheet photonic force beam can induce harmonic vibrations of illuminated microparticles (and/or nanoparticles). A phase-sensitive low-coherence optical interferometry was demonstrated on an example of a phase-sensitive spectral-domain optical coherence tomography and used to measure the nano- to sub-nano meter vibrations of microparticles. Systems and methods according to the technology disclosed in this patent document can be used for measuring biomechanics, including stiffness and viscosity, of tissues and extracellular matrix (ECM) and can provide quantitative access to physiological and pathological analysis of onset and progression of cancers for early-stage clinical diagnosis.

The mechanical properties of biomaterials are essential to their structures and functions. Especially, most biomaterials exhibit a certain extent of viscoelastic properties. The mechanical properties, including stiffness and viscosity, have been used to measure the onset and progression of tumors and exploited to quantitatively analyze various physiological and pathological states of cells. For applications in scientific, engineering and medical disciplines, there are several key characteristics that measurements of mechanical properties should possess:

(1) quantification: one of the most attractive applications of biomechanics is its capability of quantification. Therefore, precisely quantifying the mechanical properties of biomaterials are critical in mechanobiology.

(2) three-dimensional measurement: Most tissues under test are volumetric in medical analysis and three-dimensional cell-culture materials tend to better mimic biological milieu that two-dimensional materials in scientific research. Therefore, the technique developed must be capable of measuring three-dimensional biomechanics.

(3) micro-scale biomechanics: Collagens are major constituents of tissues and extracellular matrix (ECM), representing as much as 30% of total mammalian protein mass. Collagens are a type of hydrogels with micro-fiber structures. There is significant difference between macro- and micro-scale mechanical properties of hydrogels. Measuring biomechanics at micro-scale localization manner can be helpful to understand more dynamics and underlying functions of cells embedded in biomaterials.

(4) fast data acquisition: Fast measurement is also required for a dynamic monitoring of progression of tumors and cell viability. Also, it can be beneficial to the clinical trials with fast detection and diagnosis.

(5) cellular-resolution imaging and measuring biomechanics simultaneously: To reduce the complexity and avoid unnecessary additional amount of sample required, it is required that the measurement of biomechanics should be performed simultaneously with imaging at cellular-resolution.

The disclosed technology can provide one or more, or all of the characteristics listed above.

There are many techniques that have been developed for measuring mechanical properties of biomaterials. Conventional mechanical tests, such as parallel-plate oscillatory rheometry, requires bulky mechanical force applied to samples through a large area contact. Although they are easily accessible with high precision, they lack the capability of imaging and high resolution measurement. Miniaturized indentation technique, including atomic-force microscopy (AFM), can conduct high-resolution imaging and also high-performance mechanical properties measurement. But mostly, they are limited to only surfaces or two-dimensional materials. Brillouin microscopy have been developed to achieve both high resolution imaging and cellular- to sub-cellular mechanical measurement. However, the incompressibility and high water content of biomaterials are detrimental to accurate measurement of Brillouin microscopy and therefore limit their availability. Optical tweezers have been explored to be an invaluable mechanical properties measurement technique in biology. However, the prerequisite of precise optical alignment on each embedded microparticle complicates the system and limits the imaging speed due to the use of highly-focused optical trapping beam. Optical coherence elastography, combining internal or external mechanical loading with optical coherence tomography imaging modality, has been advanced to be a promising technique to obtain mechanical properties from structural deformation images with high resolution in three-dimensional materials. Currently, different mechanical loading methodologies have been proposed, including acoustic-radiation pressure, micro-tapping, compression loading, magnetomotive drive. The uses of acoustic-radiation pressure and magnetomotive drive elucidate the mechanical properties of biomaterials by measuring the shear wave propagation. Since the lack of capability of quantifying loading force in three-dimensional space, those techniques still cannot quantify the viscoelastic properties of biomaterials with high precision. Also, due to the weak focus ability, acoustic radiation pressure optical coherence elastography cannot achieve single-digit micrometer localized mechanical excitation, i.e. less than ten micrometers, and therefore obtaining micrometer scale mechanical resolution is still a challenge. Most of those optical coherence elastography techniques can only measuring the collective or macro-scale mechanical properties of biomaterials. Micro-tapping optical coherence elastography can achieve a micrometer localization mechanical excitation with high accuracy of biomechanics mapping. However, similar to AFM technique, it has been only limited to the surfaces or two-dimensional materials. Compression loading optical coherence elastography can achieve quantitative analysis of stiffness of biomaterials. However, the requirement of signal processing over a number of imaging voxels (spanning multiple coherence length of OCT source) decrease its mechanical resolution.

Compared to all the existing techniques, the technology disclosed in this patent document can provide the following unique features:

1) quantifying three-dimensional mechanical properties at micro-scale: By precisely measuring the optical force exerted on microparticles embedded in biomaterials, technology disclosed in this patent document can quantitatively reconstruct the mechanical properties of biomaterials. Since the mechanical loading is based on embedded microparticles, we can infer the micro-scale localized stiffness and viscosity of complex materials around each microparticle. The use of optical coherence elastography enables the disclosed technology to conduct large volumetric imaging and measurement.

2) high-throughput measurement in vitro and in vivo: The use of light-sheet excitation enables many microparticles to be excited simultaneously over an extended area. Without prerequisite of optical alignment, technology disclosed in this patent document can achieve a much better measurement speed over a large volume. The disclosed technology can be used for measurement and imaging both in vitro and in vivo.

3) real-time imaging and measurement of biomechanics simultaneously: The technology disclosed in this patent document is an all-optical system. The integrated system between optically mechanical loading and volumetric imaging ensures a synchronized cellular-level imaging and high-precision mechanics measurement.

4) label-free and non-destructive measurement: The technology disclosed in this patent document can provide label-free and non-destructive measurement of various samples.

Figure 2:
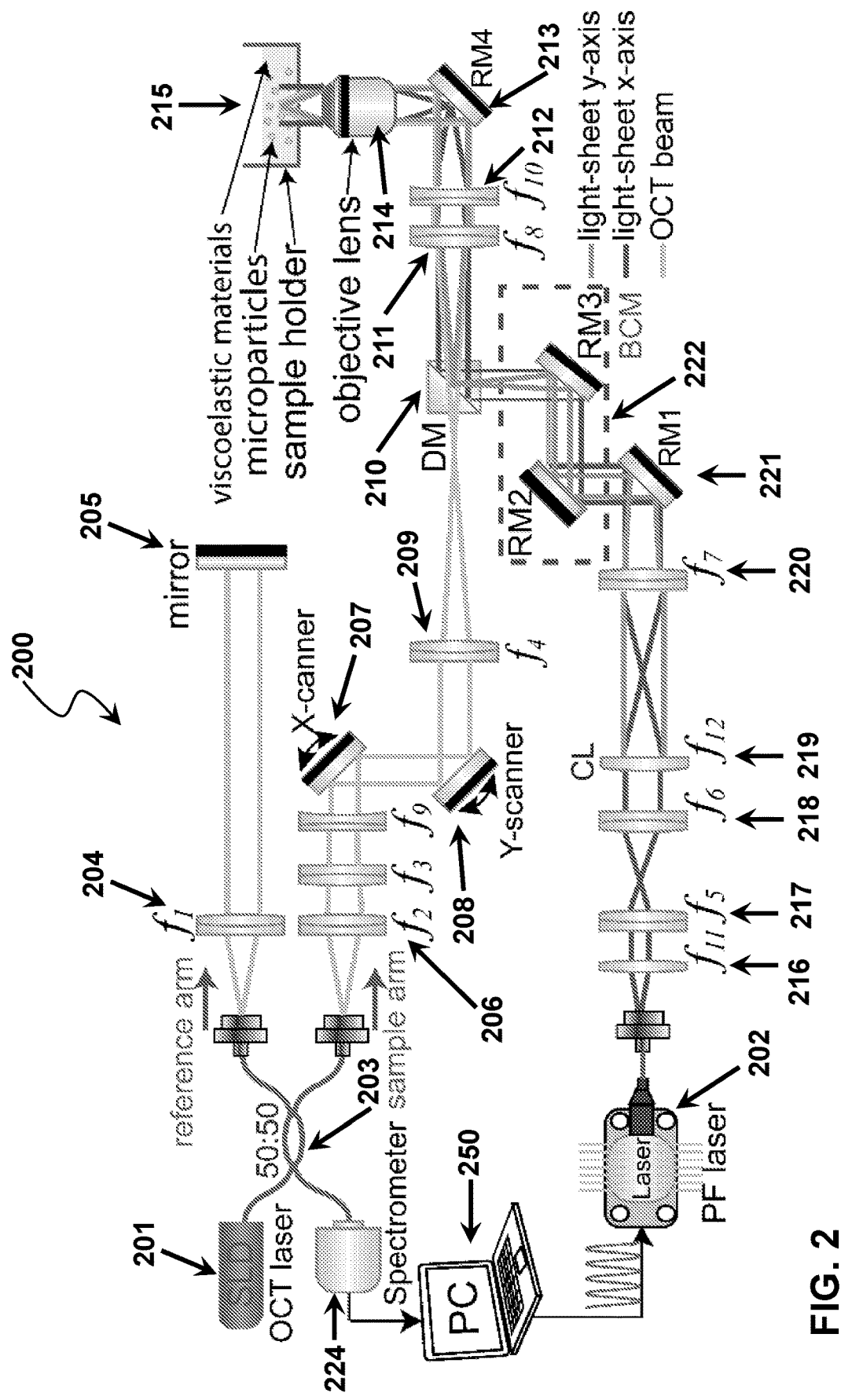
FIG. 2 shows an example of a system for implementing the system configuration in FIG. 1.

As a specific implementation of the disclosed technology, a device can be produced based on a pump-probe configuration. The pump part is a light-sheet photonic force (PF) beam section while the probe part is a low-coherence optical interferometric imaging section. FIG. 2 shows an example of an OCE system 200 for OCE measurements based on FIG. 1. The OCT light source 201 is a superluminescent laser diode with nominal central wavelength of 1300 nm and bandwidth of ~200 nm. Photonic force (PF) laser 202 is a fiber-coupled laser diode with nominal central wavelength of 789 nm. The output light from the laser 202 can be modulated at a modulation frequency in amplitude or power. In the OCT module, optical fiber paths are used to guide light in an optical interferometer configuration by using an OCT optical coupler 203: the OCT light at λ1 from the OCT light source 201 is first split by the OCT optical coupler 203 into a reference upper beam (e.g., with 50% of the total power) and an OCT sampling lower beam (e.g., with 50% of the total power) to propagate in two separate fibers. The upper fiber path forms at least part of the optical reference arm as shown to include a fiber part and a free space optical path (with a lens 204 and a reference mirror 205). The lower fiber path forms part of the sampling arm which includes a free space path that includes lenses 206, an X-scanner 207 and an Y-scanner 208 (such as, e.g., a galvo scanner) for steering the sampling beam in the x and y directions over the sample for B-scan in the OCT operation, lens 209, as well as a dichroic mirror (DM) 210 which is used to combine the scanning OCT sampling beam and the optical actuation beam into the final lens module (lens 211, lens 212, and objective lens 214) and reflector 213 for being projected onto a sample 215. The optical actuation beam from the photonic force laser source 202 at λ2 can be directed through a series of lenses 216-220, reflector 221, beam control module 222 for the optical actuation beam steering to the dichroic mirror (DM) 210. The optical actuation light-sheet can be generated by, e.g., modifying the optical phase of a Gaussian beam produced by the photonic force laser source 202 along one dimension. The phase modification can use either a spatial phase modulator or a non-symmetric optical lens. Here the use of a cylindrical lens 219 is illustrated and shown in FIG. 2 to produce an optical actuation light-sheet after the reflection mirror (RM) 213 with a collimated beam profile in the x direction and a focused beam in the y direction. Alternatively, as an example, a top-flat light-sheet beam can be generated by using a pair of aspheric lenses or by a combination of a Powell lens and an aspheric lens. For optical actuation of a sample, devices, systems and methods according to the disclosed technology can use light beams that cover extended areas of the sample and cause photonic force excitation of multiple parts of the sample simultaneously. Said parts of the sample may include particles (e.g., microparticles and/or nanoparticles) embedded in the sample as well as any other optically-scattering structures that may be included (naturally or artificially) within the sample. The returned OCT light at λ1 from the reference and sampling arms meet and optically interfere at the OCT coupler 203 to produce the OCT signal, a portion of which is coupled to the output of the optical coupler 203 which directs it to an OCT detector 224 (e.g., a Fourier domain spectrometer) which can be controlled by a personal computer (PC) 250.

In the example system in FIG. 2, the components and optical elements for generating, shaping and focusing the optical actuation light-sheet onto the sample form a separate optical system from the OCT portion of the system that includes components and optical elements for generating, shaping and focusing the OCT sampling beam onto the sample to enable separate control and adjustments of the optical actuation light-sheet and the OCT sampling beam for exerting desired optical actuation or agitation to the illuminated sheet volume within the sample. Under this design, the optical actuation light-sheet can be shaped with a desired optical intensity profile within the sheet volume in the sample for optimized optical actuation of sample tissues in order for the OCT imaging or/and fluorescence imaging to perform desired measurements. The scanning of the OCT sampling beam is controlled by a designated beam scanning module, such as the x and y scanners within the OCT optical module. Since the optical actuation light-sheet and the scanning OCT sampling beam are at different optical wavelength ranges, a dichroic mirror DM 210 can be used to combine the optical actuation light-sheet and the scanning OCT sampling beam for interacting with the sample held by the sample stage 215. In the illustrated example, the DM 210 is shown to transmit the light of the OCT sampling beam while reflecting the light of the optical actuation light sheet. Accordingly, downstream from the DM 210 to the sample stage 215, the optical actuation light-sheet and the OCT sampling beam are generally directed along a common optical path with additional beam shaping optical components such as lenses 211, 212 and an objective lens 214. The same DM 210 further allows the returned OCT sampling beam carrying with the sample information from the sample to pass through with and to be directed back to optical beam coupler 203 to spatially overlap with the returned reference beam from the reference mirror 205 to cause optical interference for OCT imaging.

Figure 3:
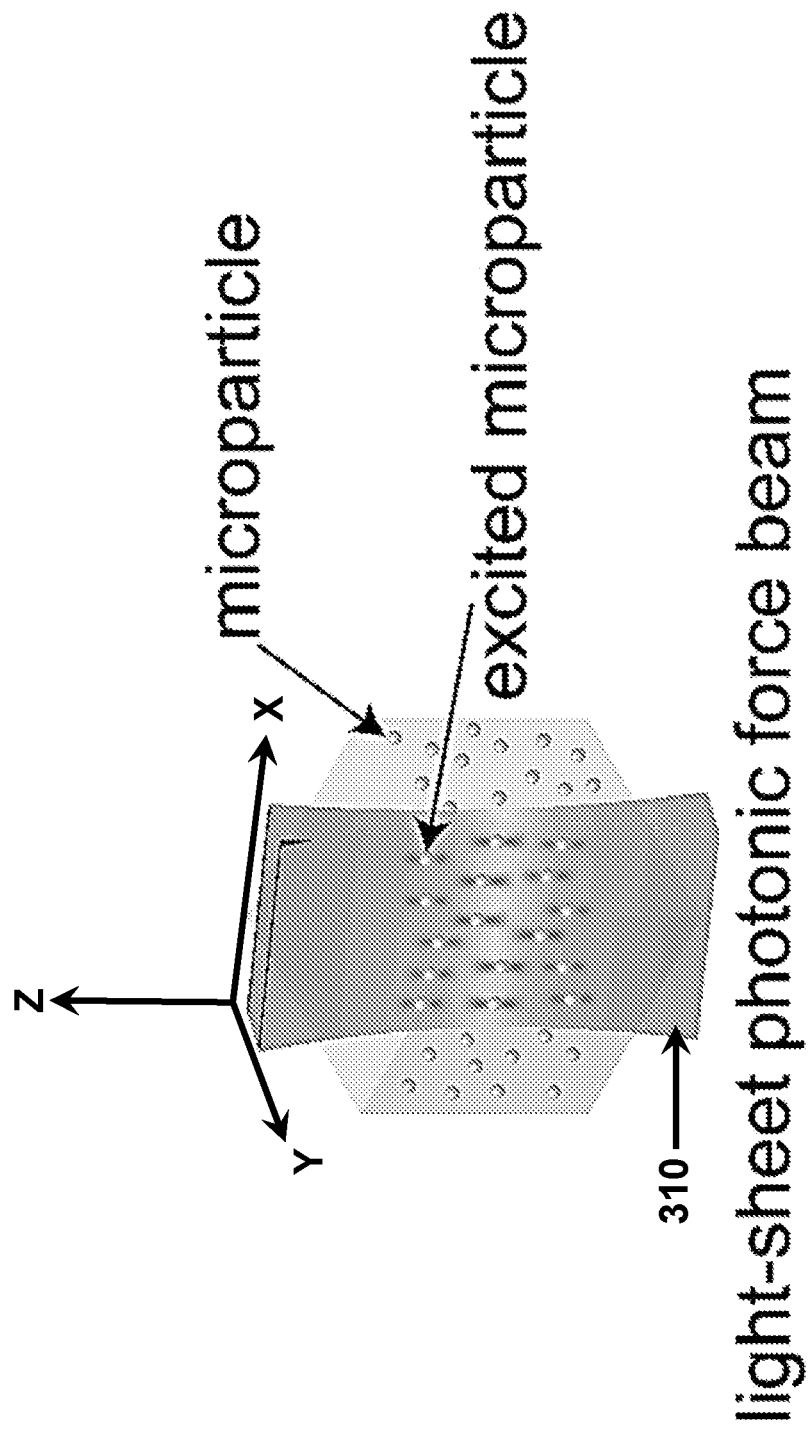
FIG. 3 shows a schematic drawing of the spatial distribution and geometry of an optical actuation light sheet.

FIG. 3 shows a schematic drawing of an optical actuation light-sheet which can be generated by systems and devices according to the disclosed technology. The optical actuation light-sheet 310 (also referred to as light-sheet photonic force (PF) beam or pump PF beam) can illuminate multiple microparticles over a certain size volume of the sample, as shown in FIG. 3. X-axis ("long" axis, also referred to as lateral axis or fast axis in OCT module) and Y-axis ("short" axis, also referred to as slow axis in OCT module) of the optical actuation light-sheet 310 are shown in FIG. 3 as well.

The pump PF beam 310 is generally a weakly-focused light-sheet which can be generated by, e.g., using a cylindrical lens (e.g., lens 219 in the system 200 shown in FIG. 2). FIG. 4A shows a measured cross-section of a light-sheet beam produced by a system according to the disclosed technology. As shown in FIG. 4A, the light-sheet has dimensions of 80 μm×1.4 μm in terms of full-width at half-maximum (FWHM) at focal plane. FIG. 4B shows a measured relative amplitude profile of a light-sheet beam. The light-sheet beam profile 410 was measured along the long axis of the beam (X-axis in FIG. 3) at focal plane while the light-sheet beam profile 420 was measured along the short axis of the beam (Y-axis in FIG. 3) at focal plane.

The light-sheet PF beam can simultaneously excite oscillations of multiple microparticles or embedded beads located along the long axis of the light sheet, thus avoiding the necessity of concurrently scanning the PF beam with OCT fast axis (which coincides with the long axis of the light sheet) and achieving a continuous single tone excitation on each bead that supports accurate quantitative mechanical reconstruction. The oscillation of beads can be probed by a phase-sensitive OCT, whose fast-axis scanning is parallel and co-aligned with the long axis of the light-sheet and, after photothermal compensation, is quantitatively correlated to micromechanical properties, elucidated as complex shear modulus $G^*=G'+iG''$, of surrounding medium in the vicinity of each bead. Sample stage or sample holder can be stepped in a direction perpendicular to the long axis of the light-sheet and fast axis of OCT imaging, functioning as the slow axis of raster scanning.

Figure 4E:
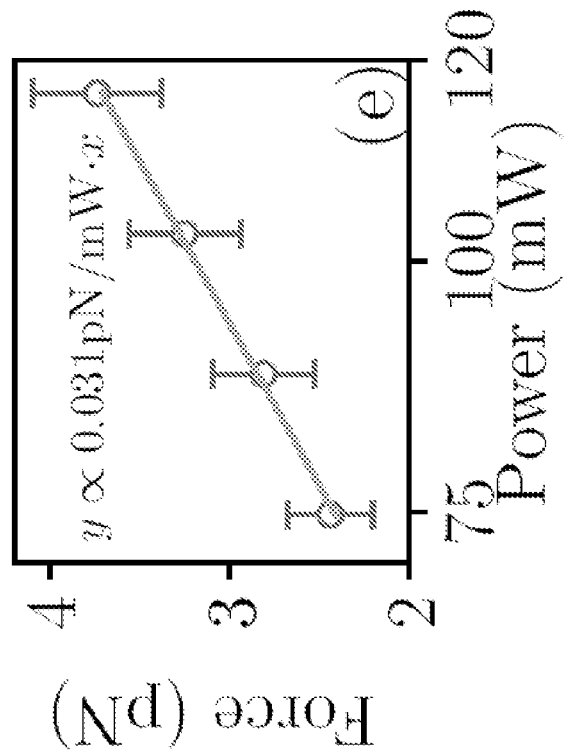
FIG. 4E shows sample measurements of a power-dependent force at the center of an optical actuation light-sheet at different optical power levels.
Figure 4D:
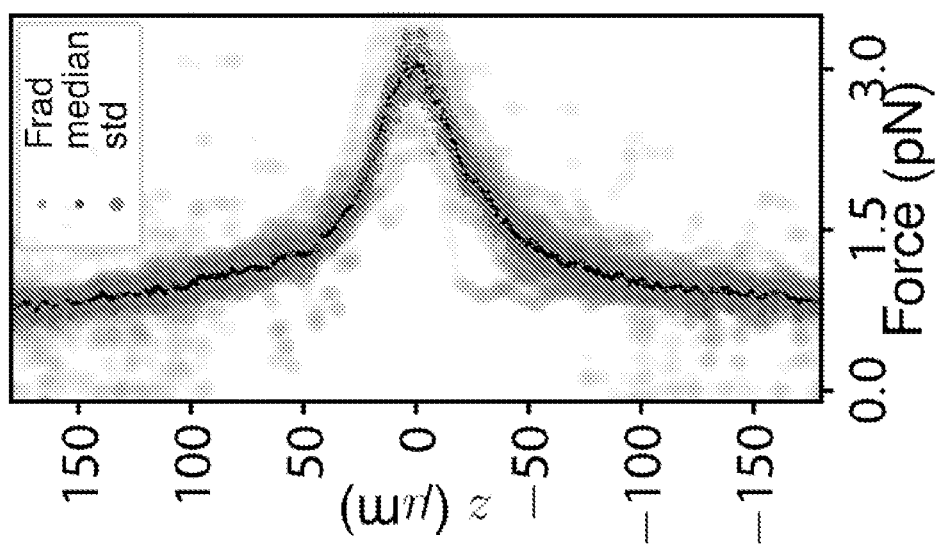
FIG. 4D shows an example of a measured depth-dependent force profile for an optical actuation light sheet.

Tracking trajectories of beads under PF beam illumination shows that both long axis and depth range of PF profile extend over ~80 μm, as shown in FIGS. 4C and 4D, with peak magnitude of force ~3.0 pN using melamine beads (refractive index n=1.68), which is ~1.5 times larger than that using polystyrene beads (n=1.58), under the illumination of 120 mW average light-sheet power incident on sample. FIG. 4C shows both measurement results as well as simulation results based on generalized Lorentz-Mie theory (GLMT). FIG. 4E shows power-dependent force measured at the center of an optical actuation light sheet.

Figure 5:
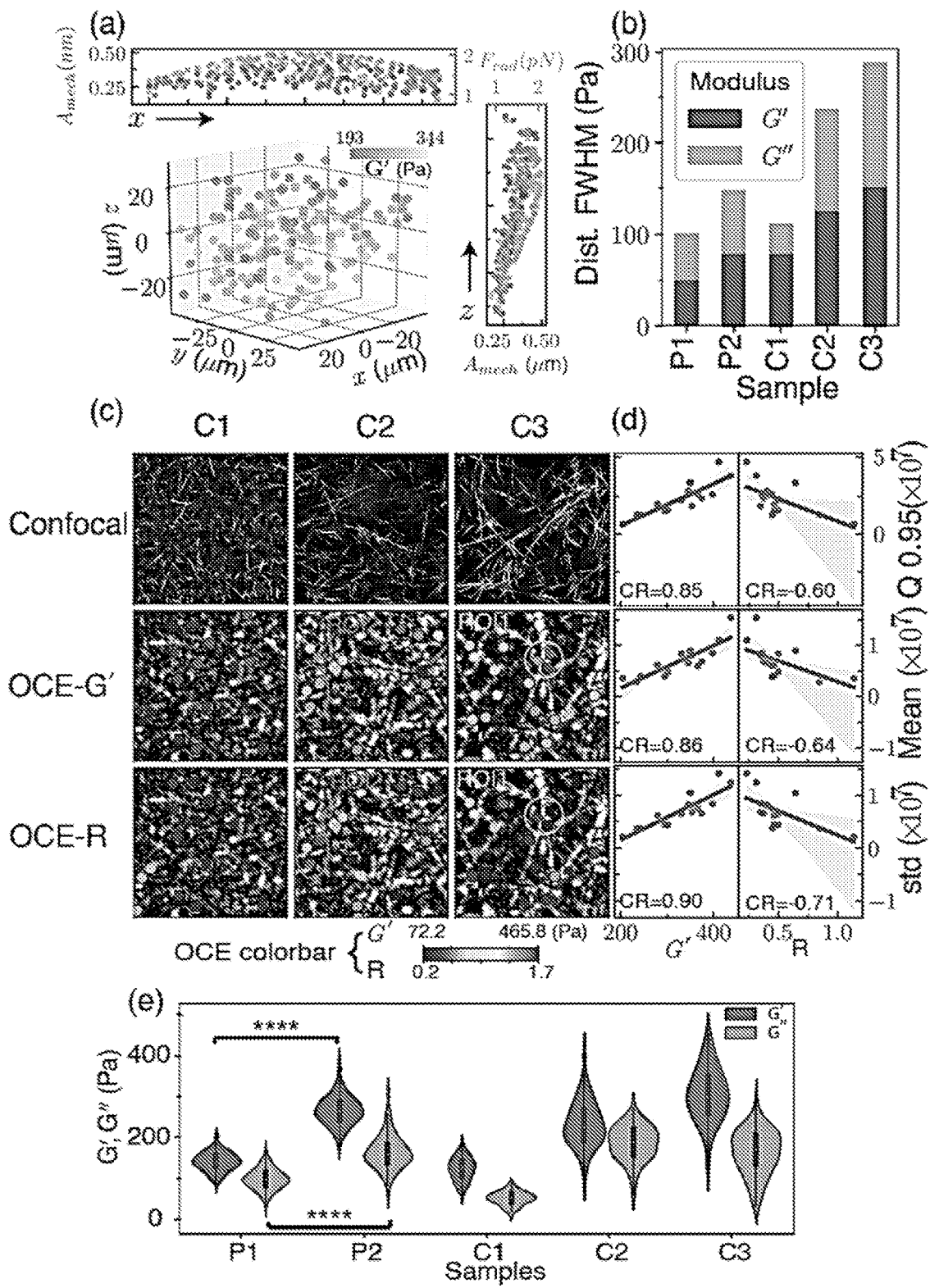
FIG. 5 illustrates examples of experimental results obtained using the technology disclosed in this patent document.

FIG. 5 illustrates some experimental results obtained using the technology disclosed in this patent document. Panel (a) in FIG. 5 shows measured bead-wise stiffness distribution in polyacrylamide (PAAm) hydrogel. Upper and left plots in panel (a) show PF and magnitude of mechanical response (Amech) with respect to spatial axis. Panel (b) in FIG. 5 shows FWHM of statistic distribution of shear modulus in different samples. Panel (c) in FIG. 5 shows bead-wise micromechanical properties in collagen samples, shown with confocal reflectance and OCT images. Panel (d) in FIG. 5 shows relationships between OCT intensity and the measured micromechanical properties in collagens. Panel (e) in FIG. 5 shows statistic distributions of micromechanics in all samples.

To validate capability of the disclosed technology of quantitative reconstruction of complex shear modulus, mechanical imaging was conducted in polyacrylamide (PAAm) hydrogels by using ~1.7 μm diameter monodisperse polystyrene beads distributed randomly over 3D with ~12 μm average spacing. The shear modulus measured using the disclosed technology agrees well with that measured by bulk rheometer. Since PAAm presents homogeneous mechanical properties, the difference between macro-scale stiffness (as determined by the bulk rheometer) and micro-scale stiffness (as determined using the disclosed technology) are trivial and also the spatial variations of bead mechanical responses correspond to spatial profile of light-sheet force (FIG. 5, panel (a)). The expected linear correlation between displacements of the beads and PF, evidenced with the lack of correlation between measured stiffness and cumulative scattering intensity, suggests that the performed measurements of $G^*$ were not significantly affected by the scatterings of embedded beads. The statistical test (p<0.0001, FIG. 5, panel (e)) also indicates that the technology disclosed in this patent document can quantitatively distinguish two samples with different mechanical properties.

To illustrate the capability of the disclosed technology in measuring micromechanics, mechanical imaging on three collagen matrices (C1 to C3) prepared with different polymerization protocols was performed, intended to produce different microstructural fibrous architectures embedded with ~1.9 μm monodisperse carboxylate-functionalized melamine-resin beads. The use of melamine beads with high refractive index ensures higher scattering signal and larger PF compared with polystyrene beads and is necessary in stiffer samples consisting of collagen microfibrous network as high scattering background. The degree of heterogeneities (shown in images from confocal reflectance microscopy in FIG. 5, panel (c)) could manifest as various degrees of elasticity G' and viscosity R=G''/G'. C1 tends to show more homogeneities (uniform distribution of G' and R as shown in OCE images of FIG. 5, panel (c)) among three collagen samples, presumably for the reason that its collagen fiber architectures are thin, short and also uniformly distributed, those have weak influence on local micromechanics (see confocal images in FIG. 5, panel (c)). C2 and C3 tends to show much more significant heterogeneities (non-uniform distribution of G' and R, see OCE images in FIG. 5, panel (c)) with existence of localized dense fibrous network where thick and long microfibrous strands dominate local micromechanics, which is shown in FIG. 5, panel (c). More interesting in OCE measurements, G'' tends to show opposite heterogeneities of R in both C2 and C3. For example, region of interest 1 (ROI1 in FIG. 5, panel (c)) appears to be more elastic (large G') and less viscous (small R) where beads are attached to a thick fiber strand and its mechanical response is dominated by microfibrous network in its vicinity. Region of interest 2 (ROI2 in FIG. 5, panel (c)) demonstrates an opposite results where the absence of clearly resolvable fiber strands results in more compliant (small G') and viscous (large R) response. The measured micromechanics could also be quantitatively correlated to the presence of localized microstructural architecture in collagen matrices, as appeared on the OCT image of FIG. 5, panel (d). The standard deviation, mean and 95% quantile of OCT scattering intensity within a local spherical volume (3 μm radius from bead circumference) around each bead quantize the presences of collagen fiber in the vicinity of probing beads. The measured local elasticity G' are strongly correlated to those parameters with correlation (CR) coefficients no less than 0.85. The degrees of mechanical heterogeneities of samples could also be quantitatively described by the FWHM of distributions of measured micromechanics, as shown in in FIG. 5, panel (b). As expected, collagen matrices with dense localized microstructural network (C2 and C3) tend to show a larger FWHM in both G' and R compared with that in C1 and PAAm. The mechanical imaging in collagen matrices demonstrates the capability of the disclosed technology to quantitatively map micromechanics which is highly correlated to local microstructural fibrous architecture.

Figure 6:
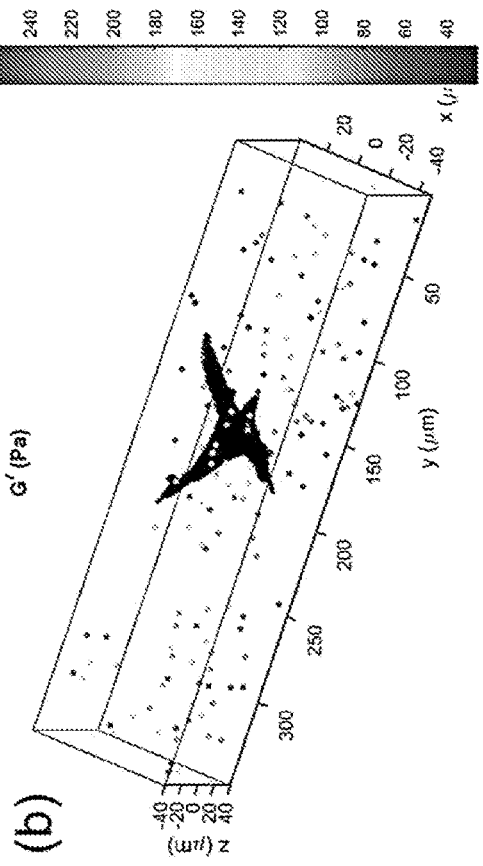
FIG. 6 illustrates examples of experimental results obtained for an engineered cellular system using the technology disclosed herein.
Figure 6:
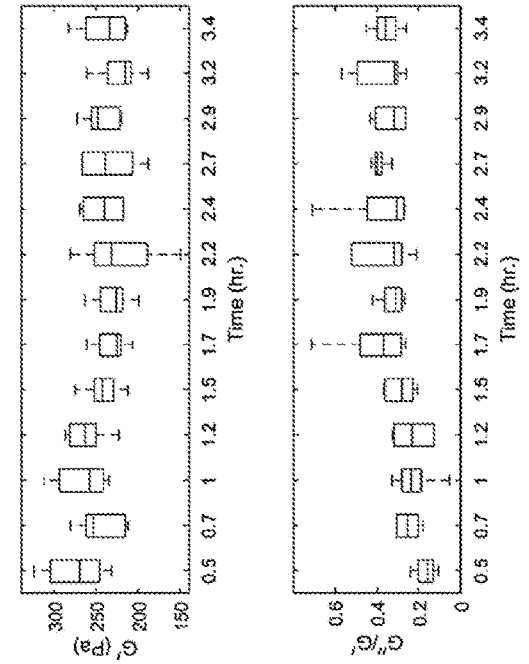
Figure 6:
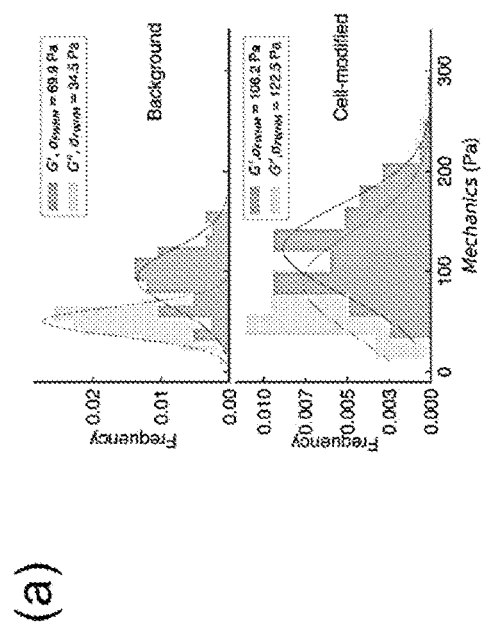
Figure 6:
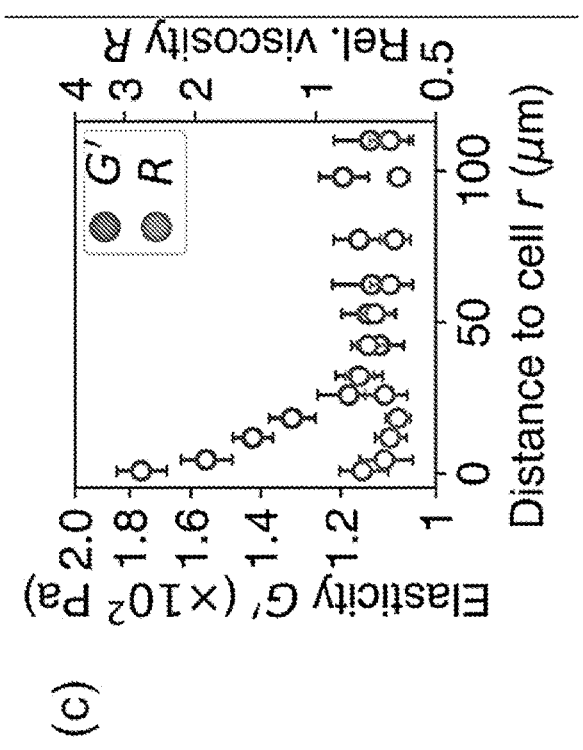

FIG. 6 illustrates some experimental results obtained for an engineered cellular system using the technology disclosed herein. Panel (a) in FIG. 6 shows micromechanics difference between ECM with and without a cell. Panel (b) in FIG. 6 shows bead-wise stiffness distribution around the cell. Panel (c) in FIG. 6 shows dependence of the micromechanics gradient on the measurement location with respect to the cell body. Panel (d) in FIG. 6 shows micromechanics changes over time, measured right after applying cytochalasin D (cytoD).

Micromechanical imaging was conducted on engineered cellular system to map the increased heterogeneities induced by cell-ECM interactions. FIG. 6, panel (a) shows a significant increase in FWHM of micromechanics distribution between with and without cell included in the ECM, implying cell induced increased micromechanical heterogeneities in ECM. Micromechanical imaging was also conducted over a large FOV (350 μm×80 μm×80 μm in y×x×z) around the cells. FIG. 6, panel (b) shows bead-wise stiffness distribution around a NIH-3T3 fibroblast cell. Beads close to the cell body present increased stiffness compared with that far away from the cell body. When combining multiple cells (here N=8), FIG. 6, panel (c) clearly shows that there is an exponential decay of stiffness when the measured position of beads distancing from cell body, indicating that cell might play an important role in remodeling the ECM. After applying cytochalasin D (CytoD) inhibitor to suppress cell contractile forces exerted on surrounding ECM, the stiffness around cell body tends to decline as shown in FIG. 6, panel (d), implying that cell might remodel local ECM by exerting contractile forces. In cell experiments, it was demonstrated that the technology disclosed in this patent document has capabilities for conducting three-dimensional micromechanical imaging over a large FOV and also imaging dynamics of cell-ECM interactions with high temporal resolution.

The technology disclosed in this patent document can be applied to either living/cellular systems (e.g., live cells or tissues) or engineered materials (such as, e.g., hydrogels). In the living/cellular systems a concentration limit for the microparticles or nanoparticles that are embedded into the system can be generally in a range from about 10' volume fraction to about $10^{-3}$ volume fraction to keep the cells in the system viable. The micro/nano particles used in the methods, systems and devices according to the disclosed technology, can be from 10s of nanometers up to several microns in size. It is also possible to use nano/microparticles having two or more different sizes. Sizes of the particles can be described, e.g., by a size distribution. Note that there isn't a constraint on the particles' size being above the optical limit so the particles could be either above the optical (e.g., visible) limit or below the optical limit or both above and below the optical limit in the case of using particles having various sizes.

Figure 7:
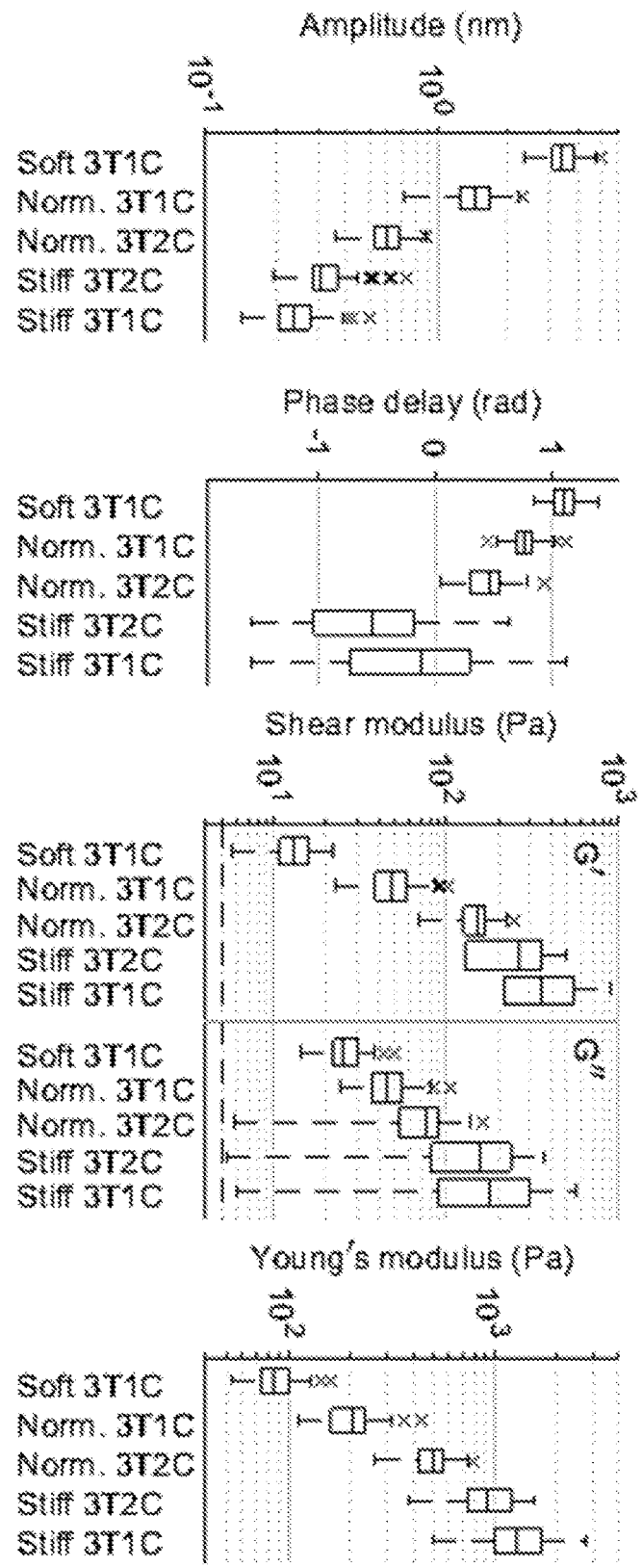
FIG. 7 shows examples of reconstructed mechanical properties of polyacrylamide (PAAm) hydrogels based on the disclosed technology.
Figure 8:
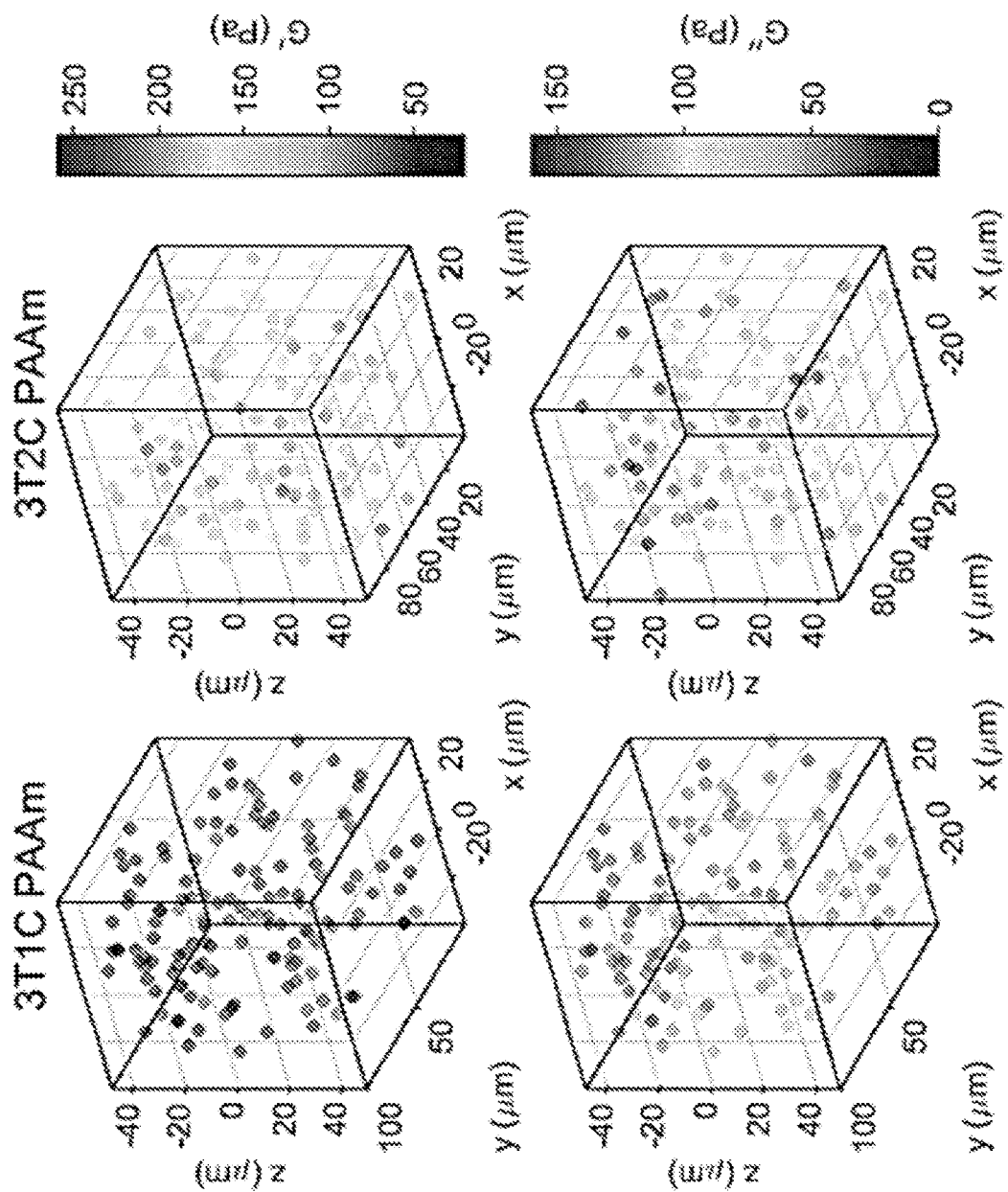
FIG. 8 shows examples of reconstructed three-dimensional mechanical properties of PAAm based on the disclosed technology.

FIG. 7 shows reconstructed mechanical properties of polyacrylamide (PAAm) hydrogels. 3T1C indicates that the total polymer concentration is 3% while the relative cross-linker concentration is 1%. Generally, in FIG. 7, nTmC indicates that the total polymer concentration is n % while the relative cross-linker concentration is m %. FIG. 8 shows reconstructed three-dimensional mechanical properties of PAAm.

As mentioned above, in order to reduce complexity and avoid unnecessary additional amount of sample required, it would be beneficial to perform measurements of biomechanics simultaneously with imaging at cellular-resolution.

The optical coherence elastography (OCE) devices according to the technology disclosed in this patent document can be integrated, e.g., with fluorescence microscopy systems and devices to provide a versatile imaging platform providing both biomechanics measurement and optical imaging capabilities. The fluorescence microscopy systems and devices used in such a platform can be based on, for example, confocal laser scanning microscopy or light-sheet microscopy. Generally, the versatile imaging platform consists of a light-sheet photonic-force OCE sub-system according to the disclosed technology that is used for mechanical imaging purpose and a fluorescence microscopy sub-system providing more specified structural details in biopolymer systems and unveiling extra knowledge of molecular mechanics related to cell-ECM biophysical interactions. Fluorescence microscopy provides additional molecular-specified understanding to cell-ECM interactions with cellular/sub-cellular resolution. It can be beneficial to correlate ECM micromechanical properties, characterized by OCE methods and systems according to the disclosed technology, to cellular metabolisms and signal pathways, imaged using fluorescence microscopy.

Figure 9:
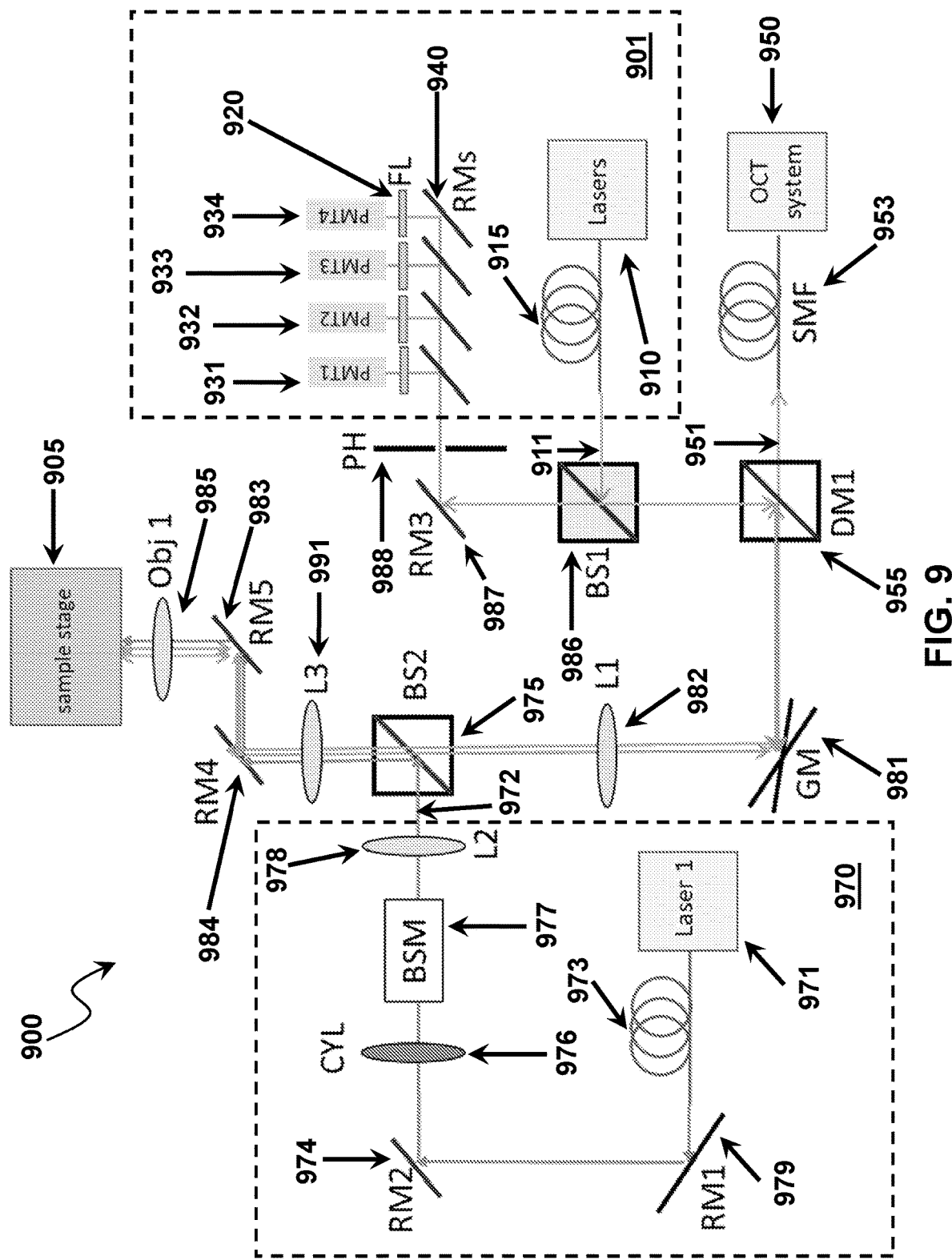
FIG. 9 shows an example of a photonic-force assisted optical coherence elastography (OCE) system based on the disclosed technology that is integrated with a confocal fluorescence microscopy system.

FIG. 9 shows an example of an OCE system according to the disclosed technology integrated with a confocal microscopy module to provide a platform 900 for co-registered light-sheet PF-OCE and confocal fluorescence microscopy measurements. As shown in FIG. 9, a confocal microscopy module 901 of the platform includes a light source 910 for fluorescence excitation of a sample held on a sample stage 905, a filter (FL) or a filter array 920, and photomultiplier tubes 931-934. The light source 910 can be, for example, a combination of multiple fluorescence excitation laser sources. The wavelength choices are dependent on the specific applications and typically are at wavelengths of 405, 488, 561, and 640 (nm). All fluorescence excitation beams are steered and combined into a single mode fiber 915 for convenience of further co-alignment with other beams. The confocal microscopy module 901 can also include, for example, an array of reflecting mirrors (RM) 940 to direct the fluorescence emission coming from the sample to the photomultiplier tubes through the array of filters 920.

As shown in FIG. 9, the platform 900 also includes an optical coherence tomography (OCT) imaging system 950 that, similar to the system shown in FIG. 2, can include an OCT light source, and OCT module, and an OCT detection and processing module. In FIG. 9, only the OCT sampling beam is shown as an optical output beam to the single mode fiber (SMF) line 953 towards the sample stage 905 and the returned OCT sampling beam from the sample is represented by the arrowed line 951 which is combined with the OCT reference beam within the OCT system 950. As shown in FIG. 9, sampling arm of the OCT imaging system shares at least a part of the optical path to the sample after the dichroic mirror (DM) 955 with the light generated by the light source 910 of the confocal microscopy module 901 of the platform. Other configurations are possible where the sampling beam of the OCT imaging system uses its own path to the sample that is separate from the path of the light from the light source 910. Nevertheless, a common feature of these configurations consists in that the sampling beam of the OCT system 950 and the light beam from the light source 910 of the confocal microscopy module 901 illuminate a common area or a common volume of the sample. As shown in FIG. 9, the sampling arm of the OCT system 950 includes a single mode fiber (SMF) 953 that provides a part of the optical path for the sampling beam of the system 950.

As further shown in FIG. 9, the platform 900 also includes an optical actuation module 970 that, similarly to the optical actuation module 130 of the system 100 shown in FIG. 1 performs optical actuation of the sample. As shown in FIG. 9, an optical actuation beam 972 produced by the module 970 joins the optical paths of the sampling beam provided by the OCT system 950 as well as the light beam generated by the light source 910 of the confocal microscopy module 901 of the platform after the beam splitter (BS) 975. Lines 911, 951, and 972 in FIG. 9 indicate the optical paths of fluorescence excitation/emission, OCT imaging, and photonic force (PF) beams, respectively. Alternatively, the module 970 can provide an optical actuation beam to the sample via an optical path that is independent from any of the optical paths of the beams from the light source 910 and/or the OCT system 950. Importantly, the optical actuation beam 972 produced by the module 970 illuminates at least a part of the area or volume of the sample that is illuminated by the sampling beam of the OCT system 950 and the light beam from the light source 910. Similarly to the optical actuation beams produced in the systems 100 and 200, the optical actuation beam generated by the optical actuation module 970 can cover an extended area of the sample and cause photonic force excitation of parts of the sample covered by the optical actuation beam simultaneously. For example, the optical actuation beam can be a light-sheet optical actuation beam as described in this patent document. Furthermore, spectral content of the optical actuation beam generated by the optical actuation module 970 can be different from the spectral content of the sampling beam of the OCT system 950 and/or the light beam from the light source 910 of the confocal microscopy module 901. In some implementations, the optical actuation beam generated by the optical actuation module 970, the sampling beam of the OCT system 950 and/or the light beam from the light source 910 can have overlapping spectral contents.

Light source 971 in FIG. 9 produces the photonic force beam, which may be around near-infrared wavelength (e.g., 780 nm) in some implementations. The output beam of the light source 971 is steered by a pair of right-angle mirrors 979 (RM1) and 974 (RM2) and passes through a cylindrical lens 976 (CYL) to generate a light-sheet PF beam. The beam steering module 977 (BSM) provides additional flexibility of beam steering for co-alignment between PF beams and other imaging beams. The light-sheet PF beam is then magnified or de-magnified by a telescope system (lenses 978 (L2) and 991 (L3)). As shown in FIG. 9, the optical actuation module 970 also includes a single mode fiber 973.

A beam splitter 986 (BS1) is used to decouple fluorescence excitation and de-scanned fluorescence emission beams from the sample. A dichroic mirror 955 (DM1) is used to combine OCT beams and fluorescence beams. Both OCT and fluorescence excitation beams can be reflected by a pair of galvo-scanning mirrors 981 for raster imaging scanning and then pass through a telescope (lens 982 (L1) and lens 991(L3)).

The light-sheet PF beam is combined with OCT and fluorescence beams at the beam splitter 975 (BS2). All beams are steered by a pair of right-angle mirrors 984 (RM4) and 983 (RM5) to pass through an objective 985 (Obj 1) and then launched into the sample. Both fluorescence emission and OCT imaging beams reversely propagate back to galvo-scanning mirrors 981 and then are decoupled at DM1 955. The OCT imaging beam propagates back into the single mode fiber 953 and then to a spectrometer to form an interference pattern with OCT reference arm of the system 950 for coherent imaging. The fluorescence emission beams pass through a right-angle mirror 987 (RM3) and a pin-hole 988. Several right-angle mirrors (RMs) 940 are used to split the fluorescent light from the sample into different fluorescent light beams. The RMs 940 include optical beam splitting reflectors which partially transmit a portion of the light and partially reflect the light. As shown, the first three RMs 940 are such optical beam splitting reflectors and the RM 940 at the far right hand side is a mirror. The different fluorescent light beams are directed to pass a set of fluorescence filters 920 which are optical bandpass filters with different center transmission optical wavelengths so that the transmitted fluorescent light beams from the different fluorescence filters 920 are centered at different optical wavelengths. A set of different optical detectors 931-934, such as photo-multiplier tubes (PMTs) are placed in the optical paths of the transmitted fluorescent light beams from the different fluorescence filters 920 for fluoresce detection. Three-dimensional fluorescence microscopy imaging can be achieved using translational movement along the optical propagation direction (Z-step) of a motorized sample stage 905.

Figure 10A:
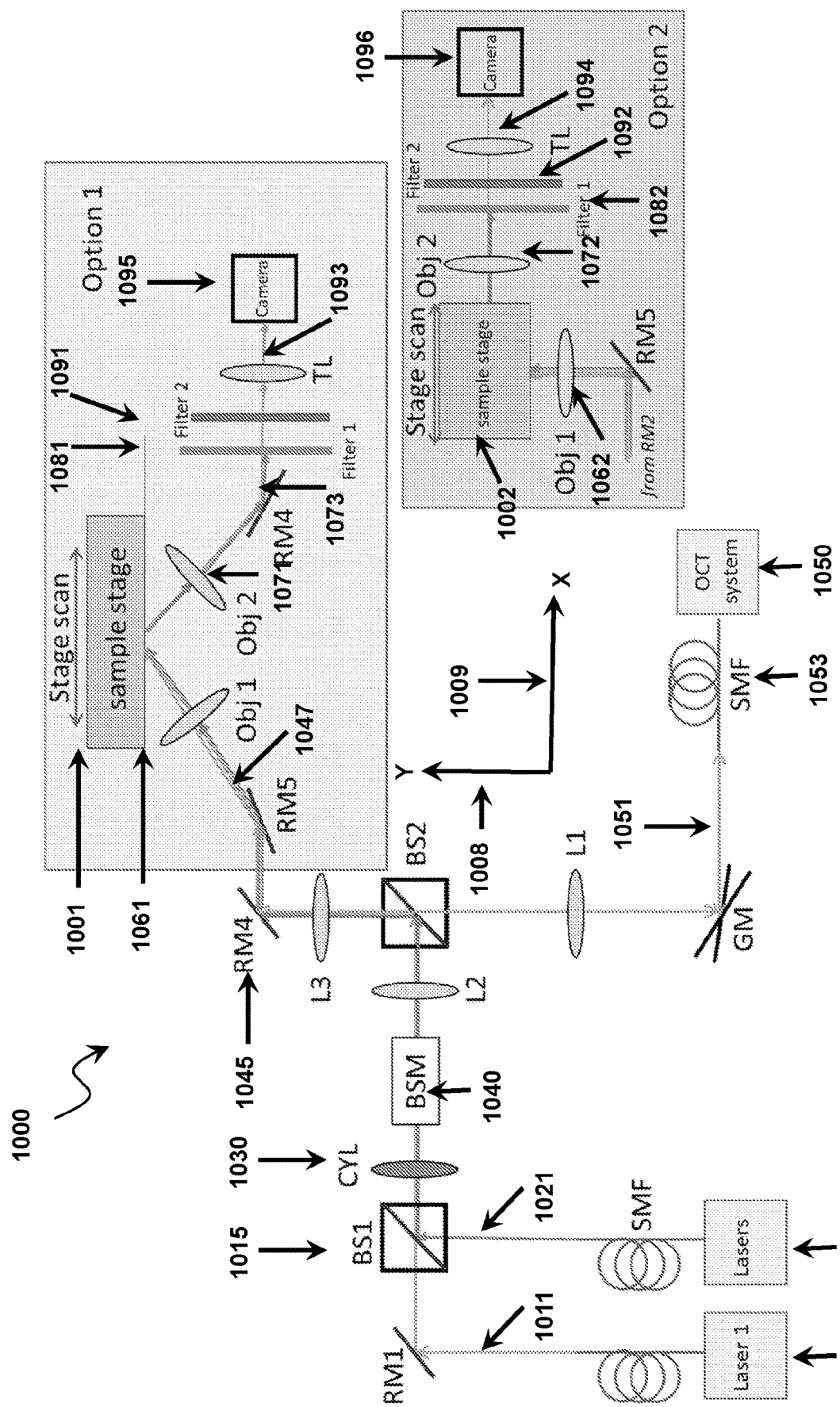
FIG. 10A shows an example of another photonic-force assisted optical coherence elastography (OCE) system based on the disclosed technology that is integrated with a light-sheet fluorescence microscopy system.

FIG. 10A shows an example of an OCE system according to the disclosed technology integrated with a light-sheet fluorescence microscopy system. In FIG. 10A, "Laser 1" 1010 is a fluorescence laser source that can emit light on a combination of multiple wavelengths (e.g., a multi-color fluorescence excitation laser source). "Lasers" 1020 is a photonic-force laser source. Light beams produced by the light sources 1010 and 1020 are combined using a beam splitter 1015 (BS1). Both the PF beam and fluorescence excitation beams share a common path to generate light-sheet beams. "CYL" 1030 is a cylindrical lens used to generate light-sheet beams both for the fluorescence excitation and photonic-force actuation. Beam steering module (BSM) 1040 is used for co-alignment of the fluorescence excitation and photonic-force beams. "OCT system" 1050 is a phase-sensitive OCT imaging system, as described in this patent document. A pair of right-angle mirrors 1045 (RM4) and 1047 (RM5) is used to steer all beams (fluorescence, photonic force, and OCT sampling) into an illumination objective (Obj 1), forming an angle relative to the horizontal surface of a sample positioned on a sample stage (1001 or 1002). "Obj 1" (1061 or 1062) is an illumination objective while "Obj 2" (1071 or 1072) is a fluorescence emission collection objective. Low-pass "Filter 1" (1081 or 1082) is used to reject residual photonic-force laser beam and OCT imaging beam while "Filter 2" (1091 or 1092) is a motorized filter wheel used to select desired wavelength channel for fluorescence imaging. "TL" (1093 or 1094) is a lens with a tunable focal length (e.g., an electrically tunable lens) used to conjugate the focal plane of fluorescence emission to a camera (1095 or 1096) which can, for example, produce spatial images of the fluorescence emission from the sample.

Inserts "Option 1" and "Option 2" in FIG. 10A demonstrate that examples of two optical configuration options (Option 1 and Option 2) can be provided for the parts of the system 1000 containing the illumination and fluorescence collection objectives "Obj 1" and "Obj 2" of the system, both of the options have a bottom-up design, as shown in FIG. 10A. Option 1 is an open-top light-sheet microscopy configuration with both objectives ("Obj 1" and "Obj 2") located on the bottom of the sample stage 1001. In Options 1 and 2, objectives "Obj 1" and "Obj 2" can be perpendicular to each other or cross at some other angle. Note that in Option 1, the optical actuation light-sheet enters the sample stage 1001 at some angle relative to the Y-axis 1008 of the stage such that the plane of the light-sheet is tilted with respect to the Y-axis (oblique-plane light-sheet fluorescence microscopy) while in Option 2 the optical actuation light-sheet enters the sample stage 1002 perpendicular to the sample stage plane in a direction that is substantially colinear with the direction of the Y-axis 1008 of the stage. The OCT beam is reflected from the sample and reversely propagates back to the single mode fiber (SMF) 1053 to form an OCT image. The fluorescence emission beams are collected by a collection objective "Obj 2" (1071 or 1072) and steered (e.g., using reflecting mirror 4 (RM4) 1073 in Option 1) into the detection camera (1095 or 1096). Lines 1011, 1051, and 1021 in FIG. 10A indicate the optical paths of fluorescence excitation/emission, OCT imaging, and photonic force (PF) beams, respectively.

Figure 10B:
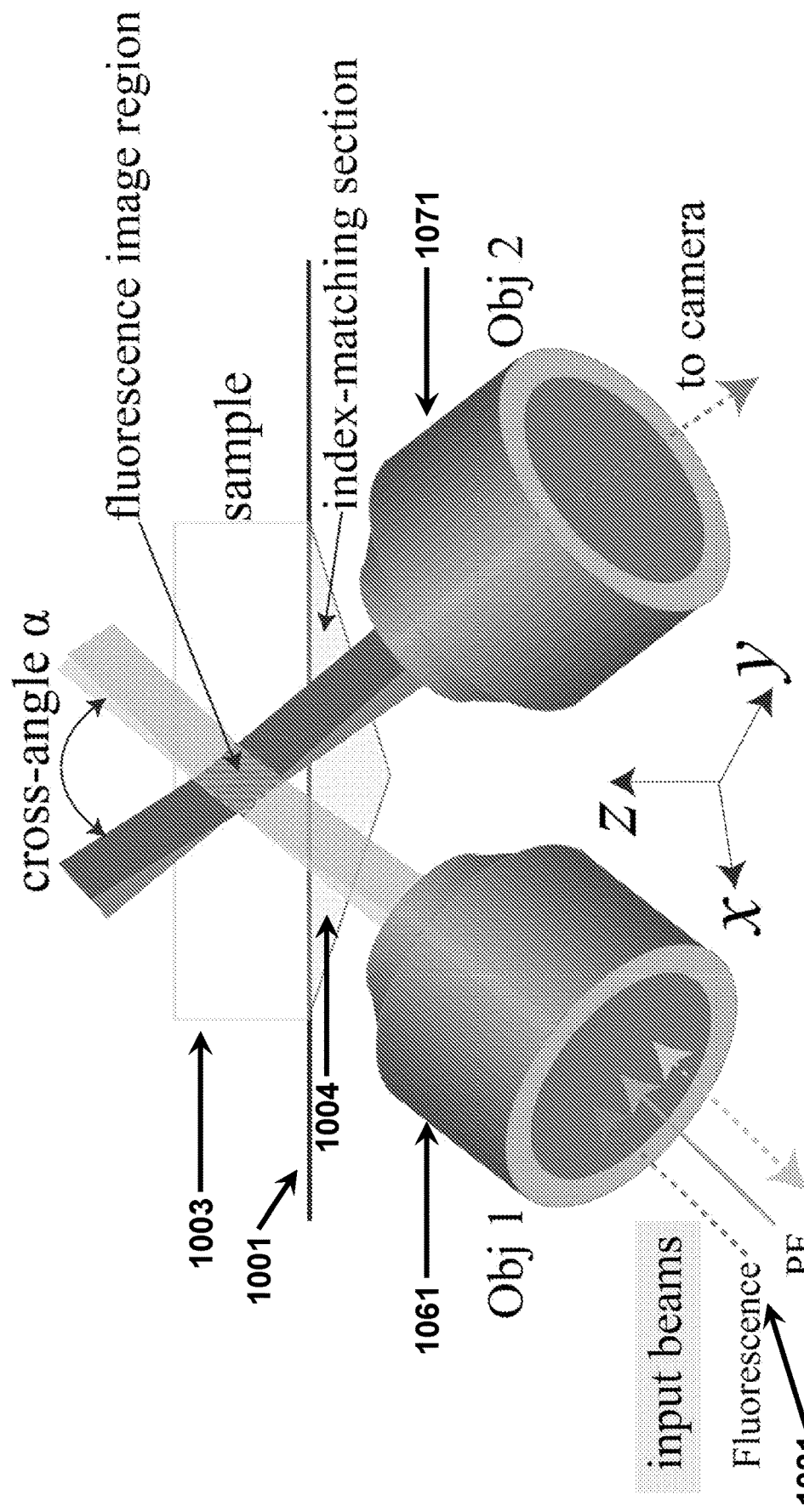
FIG. 10B illustrates an example of an implementation of the optical module that couples different input optical beams to a sample for exerting a photonic force on the sample while performing both fluoresce imaging and photonic-force assisted optical coherence elastography (OCE) measurements.

FIG. 10B illustrates an example of an optical objective lens module corresponding to the "Option 1" shown in FIG. 10A for coupling the photonic force beam, the OCT sampling beam and the fluorescent probe beam to and from the sample 1003, This optical objective lens module includes illumination objective 1061 (Obj 1) for directing all three beams to the sample 1003 and for collecting returned OCT sampling light from the sample, and fluorescence emission collection objective 1071 (Obj 2) for collecting sample emitted fluorescent light as part of the fluorescence microscopy. As shown in FIG. 10B, all input beams, including OCT (1051), PF (1011) and fluorescence excitation (1021) beams, are launched into the sample 1003 through the objective 1061. An index-matching section 1004 is used to mitigate the index mismatch induced aberrations. Typically, a glass prism is used for index matching. The generated fluorescence excitation and PF light-sheet beams are overlapped on XZ plane. The main axes of objectives 1061 and 1071 form a cross angle α, which is typically <90°. The focal planes of objectives 1061 and 1071 overlap and objective 1071 can collect fluorescence emission signals from light-sheet imaging planes of objective 1061. The collected fluorescence emission signals are relayed into an imaging camera (e.g., camera 1095 shown in FIG. 10A) after passing through an optical filter wheel and an electrically tunable lens (e.g., filter 1091 and lens 1093 shown in FIG. 10A). OCT beam is scanned along x-axis ("fast" axis) to generate XZ plane images. OCT signals originate from scattering in the sample and propagate reversely back to the OCT imaging system (e.g., the system 1050 shown in FIG. 10A). Light-sheet fluorescence microscopy can directly achieve XZ images without any scanning. To achieve three-dimensional imaging, sample stage 1001 holding the sample 1003 is scanned/moved along y-axis ("slow" axis). The focal plane position relative to objective 1061 is fixed and, if necessary, the electrically tunable lens (ETL) can also be used to compensate any focal plane translation induced by the sample stage scanning. To ensure the focal plane of the objective 1071 always overlaps with the objective 1061, an ETL is placed before a fluorescence imaging camera and synchronized with the stage scanning to conjugate fluorescence emission plane to the camera.

In some implementations of the disclosed technology, the light source 1010 (or the light source 910 of the system 900 shown in FIG. 9) can be, for example, a pulsed laser (e.g., a Ti: Sapphire laser emitting light at, e.g., 800 nm wavelength). In certain embodiments, the light source 1010 (or the light source 910) can provide two-photon fluorescence excitation in the sample. According to some implementations, the light source 1010 (or the light source 910) can emit light at, e.g., 1300 nm or 1650 nm wavelength. In certain embodiments, the light source 1010 (or the light source 910) can provide three-photon fluorescence excitation of the sample. Two-photon excitation provided by the light source 1010 (or the light source 910) can support label-free second harmonic generation (SHG) imaging, which is useful for imaging collagen microstructure, for example. According to some implementations, the light source 1010 (or the light source 910) can also provide third harmonic generation (THG) imaging of the sample. For example, a longer-wavelength (e.g., 1300 nm or 1650 nm) light source 1010 (or the light source 910) can support both 3-photon fluorescence imaging and label-free THG imaging. In some implementations, the light source 1010 (or the light source 910) can include a dispersion control module for pulse compression for applications in multiphoton fluorescence microscopy, for example, in order to produce close to a diffraction-limited pulse width for optimal nonlinear excitation in the sample. Additional details related to multiphoton fluorescence imaging microscopy can be found in the following papers each of which is incorporated by reference herein: 1) Truong, T. V., Supatto, W., Koos, D. S., Choi, J. M. and Fraser, S. E., "Deep and fast live imaging with two-photon scanned light-sheet microscopy", Nature methods, 8(9), pp. 757-760, (2011); 2) Wolf, S., Supatto, W., Debrégeas, G., Mahou, P., Kruglik, S. G., Sintes, J. M., Beaurepaire, E. and Candelier, R., "Whole-brain functional imaging with two-photon light-sheet microscopy", Nature methods, 12(5), pp. 379-380, (2015); 3) Mahou, P., Vermot, J., Beaurepaire, E. et al. "Multicolor two-photon light-sheet microscopy", Nat Methods 11, 600-601 (2014); 4) Adrià Escobet-Montalbán, Federico M. Gasparoli, Jonathan Nylk, Pengfei Liu, Zhengyi Yang, and Kishan Dholakia, "Three-photon light-sheet fluorescence microscopy," Opt. Lett. 43, 5484-5487 (2018).

Figure 11:
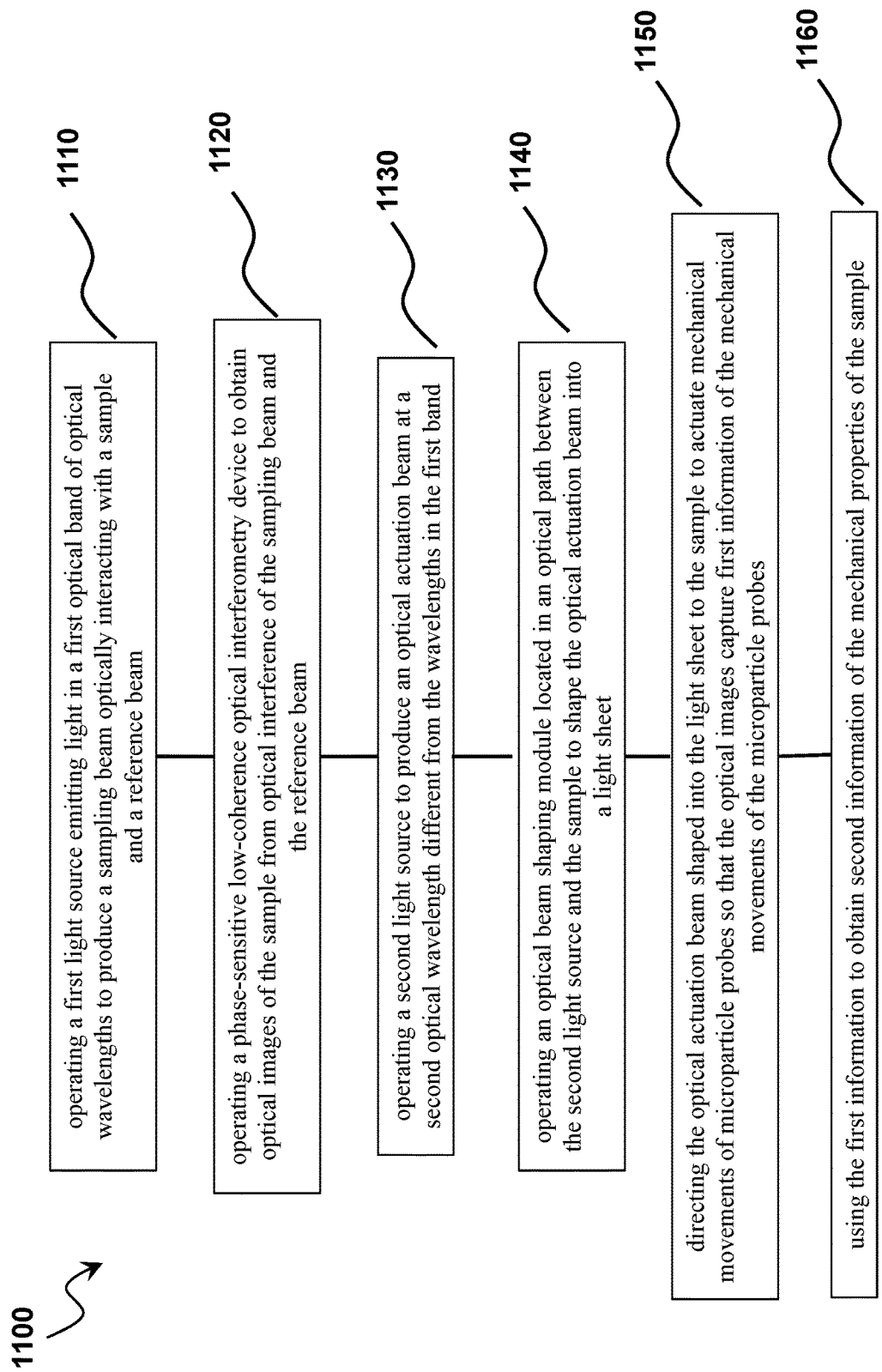
FIG. 11 illustrates an example of a method according to the disclosed technology.

FIG. 11 illustrates an example of a method 1100 of quantifying three-dimensional mechanical properties of a sample at micro-scale according to the disclosed technology. The method 1100 includes a step 1110 of operating a first light source emitting light in a first optical band of optical wavelengths to produce a sampling beam optically interacting with a sample and a reference beam, a step 1120 of operating a phase-sensitive low-coherence optical interferometry device to obtain optical images of the sample from optical interference of the sampling beam and the reference beam, a step 1130 of operating a second light source to produce an optical actuation beam at a second optical wavelength different from the wavelengths in the first band, a step 1140 of operating an optical beam shaping module located in an optical path between the second light source and the sample to shape the optical actuation beam into a light sheet, a step 1150 of directing the optical actuation beam shaped into the light-sheet to the sample to actuate mechanical movements of microparticle probes so that the optical images capture first information of the mechanical movements of the microparticle probes, and a step 1160 of using the first information to obtain second information of the mechanical properties of the sample. In some implementations, steps 1110 and 1120 are configured as an OCT imaging section while steps 1130 to 1150 are configured as a PF actuation section. According to some implementations, the OCT imaging section is implemented simultaneously with the PF actuation section to acquire the OCE information as described in the step 1160.

Figure 12:
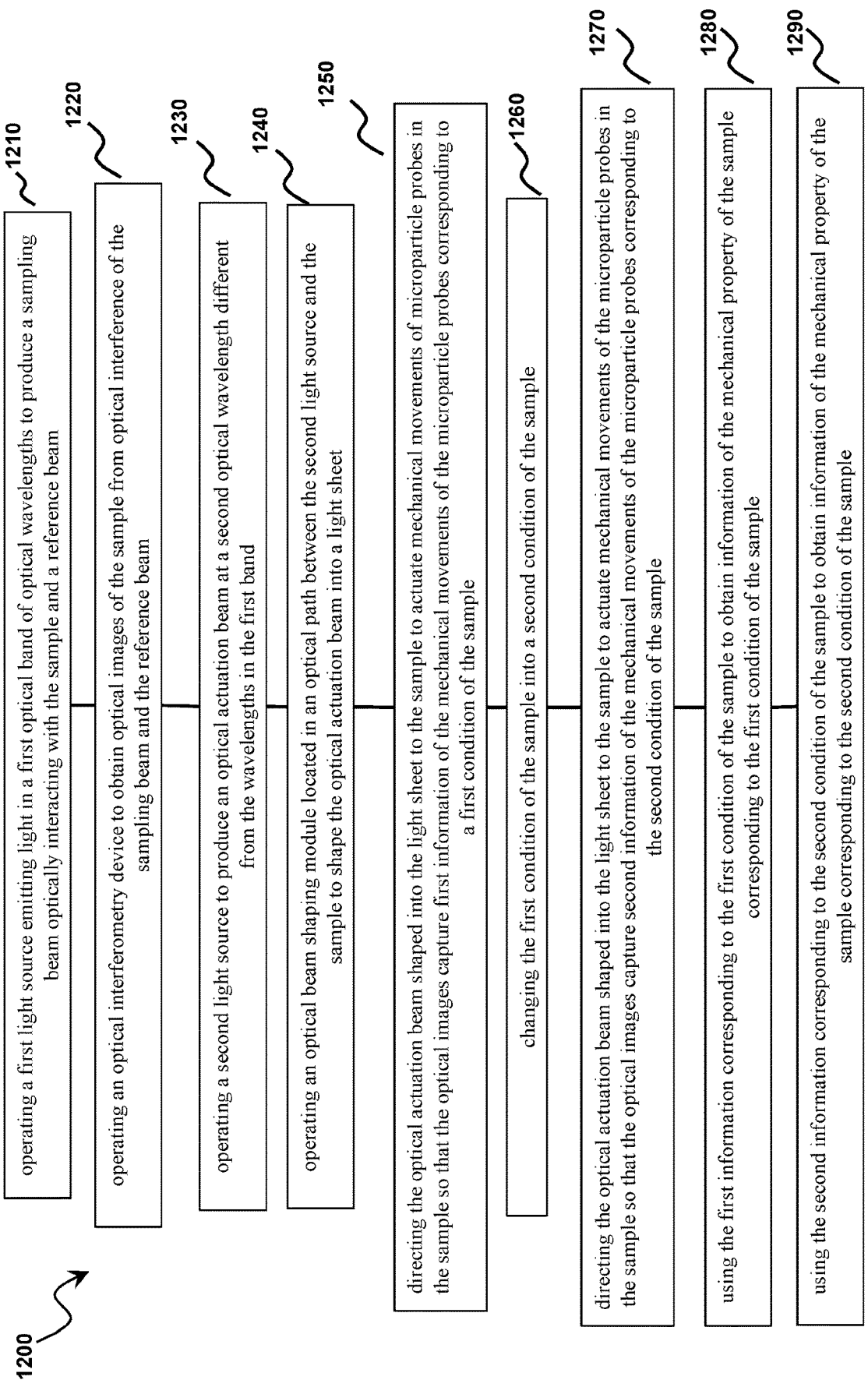
FIG. 12 illustrates an example of another method according to the disclosed technology.

FIG. 12 illustrates an example of a method 1200 of quantifying a mechanical property of a sample at microscale according to the disclosed technology. The method 1200 includes a step 1210 of operating a first light source emitting light in a first optical band of optical wavelengths to produce a sampling beam optically interacting with the sample and a reference beam, a step 1220 of operating an optical interferometry device to obtain optical images of the sample from optical interference of the sampling beam and the reference beam, a step 1230 of operating a second light source to produce an optical actuation beam at a second optical wavelength different from the wavelengths in the first band, a step 1240 of operating an optical beam shaping module located in an optical path between the second light source and the sample to shape the optical actuation beam into a light sheet, a step 1250 of directing the optical actuation beam shaped into the light-sheet to the sample to actuate mechanical movements of microparticle probes in the sample so that the optical images capture first information of the mechanical movements of the microparticle probes corresponding to a first condition of the sample, a step 1260 of changing the first condition of the sample into a second condition of the sample, a step 1270 of directing the optical actuation beam shaped into the light-sheet to the sample to actuate mechanical movements of the microparticle probes in the sample so that the optical images capture second information of the mechanical movements of the microparticle probes corresponding to the second condition of the sample, a step 1280 of using the first information corresponding to the first condition of the sample to obtain information of the mechanical property of the sample corresponding to the first condition of the sample, and a step 1290 of using the second information corresponding to the second condition of the sample to obtain information of the mechanical property of the sample corresponding to the second condition of the sample.

The disclosed technology can be used in various applications, e.g., measuring mechanical properties of extracellular matrix (ECM) or other biomaterials, especially hydrogels; quantifying mechanical properties and heterogeneity of materials used in tissue-engineering and regenerative medicine clinical applications; monitoring micro-scale localized cell-ECM interaction dynamics, revealing underlying cell functions and providing quantitative analysis of pathological and physiological cell states; observing onset and progression of transformed cancerous cells in early-stage diagnosis; measuring stiffness of tissues and its relation to drug delivery efficacy.

One aspect of the disclosed technology relates to a system for providing optical actuation and optical sensing that includes an optical coherence tomography (OCT) device that performs optical imaging of a sample based on optical interferometry from an optical sampling beam interacting with an optical sample and an optical reference beam; an OCT light source to provide an OCT imaging beam into the OCT device which splits the OCT imaging beam into the optical sampling beam and the optical reference beam; a light source that produces an optical actuation beam that is coupled along with the optical sampling beam to be directed to the sample to actuate particles or structures in the sample so that the optical imaging captures information of the sample under the optical actuation; and an optical beam shaping module located in an optical path between the light source and the sample to shape the optical actuation beam into a light-sheet to illuminate a region of the sample.

In some example embodiments of the system for providing optical actuation and optical sensing, the optical actuation beam is modulated at a modulation frequency. In certain example embodiments, the optical actuation beam is modulated in amplitude or power. In other example embodiments, the system for providing optical actuation and optical sensing includes an OCT detection and processing module that is configured to process optical imaging information from OCT device output based on varying mechanical properties of different sample materials to distinguish one sample material from another. According to certain example embodiments, the system includes an OCT detection and processing module that is configured to process optical imaging information from OCT device output based on varying optical scattering properties of different sample materials to distinguish one sample material from another. In some example embodiments, the system includes an OCT detection and processing module that is configured to process optical imaging information from OCT device output based on varying optical absorption properties of different sample materials to distinguish one sample material from another. In other example embodiments, the OCT light source is configured to provide an OCT imaging beam at an optical wavelength different from an optical wavelength of the optical actuation beam. According to some example embodiments, the system includes a scanner that is configured to scan the optical sampling beam over the sample in performing the optical imaging without scanning the optical actuation beam. In certain example embodiments, the system includes a beam guiding optics module that is configured to direct the optical actuation beam to spatially overlap with the optical sampling beam over the sample in performing the optical imaging. In other example embodiments, the optical beam shaping module includes optical lenses that include one or more cylindrical lenses. According to some example embodiments, the system includes a fluorescent excitation light source to produce a fluorescent excitation light to the sample to cause the sample to emit fluorescent light; and a fluorescent detection module located to receive the emitted fluorescent light from the sample to measure one or more properties of the sample from the emitted fluorescent light. In some example embodiments, the fluorescent detection module includes an imaging sensor (such as, e.g., a camera) to capture an optical image carried by the emitted fluorescent light from the sample in addition to an optical image produced by the OCT device. In other example embodiments, the fluorescent detection module includes: different optical filters to receive different portions of the emitted fluorescent light from the sample to filter the receive different portions to generate filtered fluorescent beams at different center optical wavelengths, respectively; and different optical detectors located to receive the filtered fluorescent beams at different center optical wavelengths, respectively, to capture sample information from the filtered fluorescent beams at different center optical wavelengths. According to certain example embodiments, the system includes an optical combiner device located downstream from the optical beam shaping module to receive the optical actuation beam from the optical beam shaping module and the optical sampling beam, the optical combiner device structured and operable to combine the optical actuation beam and the optical sampling beam to propagate along a common optical path to the sample.

Another aspect of the disclosed technology relates to a method of quantifying three-dimensional mechanical properties of a sample at micro-scale that includes operating a first light source emitting light in a first optical band of optical wavelengths to produce a sampling beam optically interacting with the sample and a reference beam, operating a phase-sensitive low-coherence optical interferometry device to obtain optical images of the sample from optical interference of the sampling beam and the reference beam, operating a second light source to produce an optical actuation beam at a second optical wavelength different from the wavelengths in the first band, operating an optical beam shaping module located in an optical path between the second light source and the sample to shape the optical actuation beam into a light sheet, directing the optical actuation beam shaped into the light-sheet to the sample to actuate mechanical movements of microparticle probes so that the optical images capture first information of the mechanical movements of the microparticle probes, and using the first information to obtain second information of the mechanical properties of the sample.

In some example embodiments of the method of quantifying three-dimensional mechanical properties of a sample at micro-scale, the method includes modulating the optical actuation beam at a modulation frequency. In certain example embodiments, the optical actuation beam is modulated in intensity or power. According to some example embodiments, modulation is performed using a modulation waveform. In some example embodiments of the method, the first information includes an amplitude of movements of the microparticle probes and a phase shift of movements of the microparticle probes with respect to the modulation waveform. According to other example embodiments of the method, the second information includes components of a complex shear modulus. In some example embodiments of the method, the shaping comprises modifying an optical phase of the optical actuation beam along an axis. In certain example embodiments of the method, the shaping comprises passing the optical actuation beam through a spatial phase modulator or a non-symmetric optical lens. According to some example embodiments of the method, the method includes steering the sampling beam over the sample so as to bring different parts of the sample into an optical contact with the sampling beam. In other example embodiments of the method, the method includes steering the optical actuation beam over the sample so as to bring different parts of the sample into an optical contact with the optical actuation beam. According to certain example embodiments of the method, the sampling beam and the optical actuation beam spatially overlap over the sample. In some example embodiments of the method, the microparticle probes comprise melamine resin beads. According to some example embodiments of the method, the microparticle probes are between 1 nanometer and 10 micrometers in diameter.

Yet another aspect of the disclosed technology relates to a system for quantifying three-dimensional mechanical properties of a sample at micro-scale that includes a first light source configured to emit light in a first optical spectral band of optical wavelengths to produce a sampling beam optically interacting with the sample and a reference beam; a phase-sensitive low-coherence optical interferometry device configured to obtain optical images of the sample from optical interference of the sampling beam and the reference beam; a second light source configured to produce an optical actuation beam in form of a sheet at a second optical wavelength different from the wavelengths in the first band, wherein the optical actuation beam actuates mechanical movements of microparticle probes so that the optical images capture first information of the mechanical movements of the microparticle probes; a processor configured to use the first information to obtain second information of the mechanical properties of the sample, a third light source that produces a fluorescent excitation light to the sample to cause the sample to emit fluorescent light, and a fluorescent detection module located to receive the emitted fluorescent light from the sample to measure one or more properties of the sample from the emitted fluorescent light.

In some example embodiments of the system for quantifying three-dimensional mechanical properties of a sample at micro-scale, the fluorescent detection module includes an imaging sensor (such as, e.g., a camera) to capture an optical image carried by the emitted fluorescent light from the sample in addition to an optical image produced by the OCT device. In other example embodiments, the fluorescent detection module includes: different optical filters to receive different portions of the emitted fluorescent light from the sample to filter the receive different portions to generate filtered fluorescent beams at different center optical wavelengths, respectively; and different optical detectors located to receive the filtered fluorescent beams at different center optical wavelengths, respectively, to capture sample information from the filtered fluorescent beams at different center optical wavelengths.

Another aspect of the disclosed technology relates to a method of quantifying a mechanical property of a sample at micro-scale that includes operating a first light source emitting light in a first optical band of optical wavelengths to produce a sampling beam optically interacting with the sample and a reference beam, operating an optical interferometry device to obtain optical images of the sample from optical interference of the sampling beam and the reference beam, operating a second light source to produce an optical actuation beam at a second optical wavelength different from the wavelengths in the first optical band, operating an optical beam shaping module located in an optical path between the second light source and the sample to shape the optical actuation beam into a light sheet, directing the optical actuation beam shaped into the light-sheet to the sample to actuate mechanical movements of microparticle probes in the sample so that the optical images capture first information of the mechanical movements of the microparticle probes corresponding to a first condition of the sample, changing the first condition of the sample into a second condition of the sample, directing the optical actuation beam shaped into the light-sheet to the sample to actuate mechanical movements of the microparticle probes in the sample so that the optical images capture second information of the mechanical movements of the microparticle probes corresponding to the second condition of the sample, using the first information corresponding to the first condition of the sample to obtain information of the mechanical property of the sample corresponding to the first condition of the sample, and using the second information corresponding to the second condition of the sample to obtain information of the mechanical property of the sample corresponding to the second condition of the sample.

In some example embodiments of the method of quantifying a mechanical property of a sample at micro-scale, the first condition of the sample is an absence of a biological cell from the sample and the second condition of the sample is a presence of the biological cell in the sample. In other example embodiments of the method, the first condition of the sample is an absence of a chemical compound from the sample and the second condition of the sample is a presence of the chemical compound in the sample. According to some example embodiments of the method, the mechanical property of the sample corresponds to a component of a complex shear modulus of the sample. In certain example embodiments of the method, the mechanical property of the sample is an elasticity of the sample. According to other example embodiments of the method, the mechanical property of the sample is a viscosity of the sample.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

It is understood that the various disclosed embodiments may be implemented individually, or collectively, in devices comprised of various optical components, electronics hardware and/or software modules and components. These devices, for example, may comprise a processor, a memory unit, an interface that are communicatively connected to each other, and may range from desktop and/or laptop computers, to mobile devices and the like. The processor and/or controller can perform various disclosed operations based on execution of program code that is stored on a storage medium. The processor and/or controller can, for example, be in communication with at least one memory and with at least one communication unit that enables the exchange of data and information, directly or indirectly, through the communication link with other entities, devices and networks. The communication unit may provide wired and/or wireless communication capabilities in accordance with one or more communication protocols, and therefore it may comprise the proper transmitter/receiver antennas, circuitry and ports, as well as the encoding/decoding capabilities that may be necessary for proper transmission and/or reception of data and other information. For example, the processor may be configured to receive electrical signals or information from the disclosed sensors (e.g., CMOS sensors), and to process the received information to produce images or other information of interest.

Various information and data processing operations described herein may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media that is described in the present application comprises non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes Only a few implementations and examples are described and other implementations, enhancements and variations can be made based on what is described and illustrated in this patent document.

What is claimed is:

1. A system for providing optical actuation and optical sensing, comprising:
   an optical coherence tomography (OCT) device that performs optical imaging of a sample based on optical interferometry from an optical sampling beam that propagates along a sampling-beam path and interacts with the sample and an optical reference beam;
   an OCT light source to provide an OCT imaging beam into the OCT device which splits the OCT imaging beam into the optical sampling beam and the optical reference beam;
   a light source that produces an optical actuation beam that propagates along an actuation-beam path before being coupled with the optical sampling beam to be directed to the sample to actuate particles or structures in the sample so that the optical imaging captures information of the sample under the optical actuation;
   an optical beam shaping module located in the actuation-beam path between the light source and the sample to shape the optical actuation beam into a light-sheet to illuminate a region of the sample;
   a fluorescent excitation light source to produce a fluorescent excitation light to the sample to cause the sample to emit fluorescent light;
   a scanner that is (i) on the sampling-beam path, (ii) not on the actuation-beam path, and (iii) scans the optical sampling beam over the sample in performing the optical imaging; and
   a fluorescent detection module located to receive the emitted fluorescent light from the sample to measure one or more properties of the sample from the emitted fluorescent light, wherein the fluorescent detection module includes:
   different optical filters to receive different portions of the emitted fluorescent light from the sample to filter the received different portions to generate filtered fluorescent beams at different center optical wavelengths, respectively; and
   different optical detectors located to receive the filtered fluorescent beams at different center optical wavelengths, respectively, to capture sample information from the filtered fluorescent beams at different center optical wavelengths.

2. The system as in claim 1, wherein the optical actuation beam is modulated at a modulation frequency.

3. The system as in claim 2, wherein the optical actuation beam is modulated in amplitude or power.

4. The system as in claim 1, further comprising an OCT detection and processing module that is configured to process optical imaging information from OCT device output based on varying mechanical properties of different sample materials to distinguish one sample material from another.

5. The system as in claim 1, further comprising an OCT detection and processing module that is configured to process optical imaging information from OCT device output based on varying optical scattering properties of different sample materials to distinguish one sample material from another.

6. The system as in claim 1, wherein the fluorescent detection module includes an imaging sensor to capture an optical image carried by the emitted fluorescent light from the sample in addition to an optical image produced by the OCT device.

7. The system as in claim 1, wherein the OCT light source is configured to provide an OCT imaging beam at an optical wavelength different from an optical wavelength of the optical actuation beam.

8. The system as in claim 1, further comprising a beam guiding optics module that is configured to direct the optical actuation beam to spatially overlap with the optical sampling beam over the sample in performing the optical imaging.

9. The system as in claim 1, wherein the optical beam shaping module includes optical lenses that include one or more cylindrical lenses.

10. The system as in claim 1, further comprising:
an optical combiner device located downstream from the optical beam shaping module to receive the optical actuation beam from the optical beam shaping module and the optical sampling beam, the optical combiner device structured and operable to combine the optical actuation beam and the optical sampling beam to propagate along a common optical path to the sample.

11. A method of quantifying mechanical properties of a sample, comprising:
operating a first light source emitting light in a first optical band of optical wavelengths to produce (i) a sampling beam that propagates along a sampling-beam path before optically interacting with the sample and (ii) a reference beam;
operating a second light source to produce an optical actuation beam, propagating along an actuation-beam path, at a second optical wavelength different from the wavelengths in the first band;
operating a phase-sensitive low-coherence optical interferometry device to obtain optical images, of the sample from optical interference of the sampling beam and the reference beam, in part by scanning, with a scanner that is (i) on the sampling-beam path and (ii) not on the actuation-beam path, the optical sampling beam over the sample without scanning the optical actuation beam;
modulating the optical actuation beam at a modulation frequency, intensity or power, using a modulation waveform;
operating an optical beam shaping module located in the actuation-beam path between the second light source and the sample to shape the optical actuation beam into a light-sheet;
directing the optical actuation beam shaped into the light-sheet to the sample to actuate mechanical movements of microparticle probes so that the optical images capture first information of the mechanical movements of the microparticle probes;
using the first information to obtain second information of the mechanical properties of the sample; and
modulating the optical actuation beam at a modulation frequency;
wherein modulation is performed using a modulation waveform, and wherein the first information includes an amplitude of movements of the microparticle probes and a phase shift of movements of the microparticle probes with respect to the modulation waveform.

12. The method of claim 11, wherein the second information includes components of a complex shear modulus.

13. The method of claim 11, further comprising steering the sampling beam over the sample so as to bring different parts of the sample into an optical contact with the sampling beam.

14. The method of claim 11, further comprising steering the optical actuation beam over the sample so as to bring different parts of the sample into an optical contact with the optical actuation beam.

15. The method of claim 11, wherein the microparticle probes comprise melamine resin beads.

16. The method of claim 11, wherein the microparticle probes are between 1 nanometer and 10 micrometers in diameter.

17. A method of quantifying mechanical properties of a sample, comprising:
operating a first light source emitting light in a first optical band of optical wavelengths to produce (i) a sampling beam that propagates along a sampling-beam path before optically interacting with the sample and (ii) a reference beam;
operating a second light source to produce an optical actuation beam, propagating along an actuation-beam path, at a second optical wavelength different from the wavelengths in the first band;
operating a phase-sensitive low-coherence optical interferometry device to obtain optical images of the sample from optical interference of the sampling beam and the reference beam, in part by scanning, with a scanner that is (i) on the sampling-beam path, (ii) not on the actuation-beam path, the optical sampling beam over the sample without scanning the optical actuation beam;
operating an optical beam shaping module located in an optical path between the second light source and the sample to shape the optical actuation beam into light-sheet;
directing the optical actuation beam shaped into the light-sheet to the sample to actuate mechanical movements of microparticle probes so that the optical images capture first information of the mechanical movements of the microparticle probes; and
using the first information to obtain second information of the mechanical properties of the sample, wherein the shaping comprises modifying an optical phase of the optical actuation beam along an axis.

18. The method of claim 17, further comprising steering the sampling beam over the sample so as to bring different parts of the sample into an optical contact with the sampling beam.

19. The method of claim 17, further comprising steering the optical actuation beam over the sample so as to bring different parts of the sample into an optical contact with the optical actuation beam.

20. The method of claim 17, wherein the microparticle probes comprise melamine resin beads.

21. The method of claim 17, wherein the microparticle probes are between 1 nanometer and 10 micrometers in diameter.

22. A method of quantifying mechanical properties of a sample, comprising:

operating a first light source emitting light in a first optical band of optical wavelengths to produce (i) a sampling beam that propagates along a sampling-beam path before optically interacting with the sample and (ii) a reference beam;

operating a second light source to produce an optical actuation beam, propagating along an actuation-beam path, at a second optical wavelength different from the wavelengths in the first band;

operating a phase-sensitive low-coherence optical interferometry device to obtain optical images of the sample from optical interference of the sampling beam and the reference beam, in part by scanning, with a scanner that is (i) on the sampling-beam path, (ii) not on the actuation-beam path, the optical sampling beam over the sample without scanning the optical actuation beam;

operating an optical beam shaping module located in an optical path between the second light source and the sample to shape the optical actuation beam into light-sheet;

directing the optical actuation beam shaped into the light-sheet to the sample to actuate mechanical movements of microparticle probes so that the optical images capture first information of the mechanical movements of the microparticle probes; and using the first information to obtain second information of the mechanical properties of the sample wherein the shaping comprises passing the optical actuation beam through a spatial phase modulator or a non-symmetric optical lens.

23. The method of claim 22, further comprising steering the sampling beam over the sample so as to bring different parts of the sample into an optical contact with the sampling beam.

24. The method of claim 22, further comprising steering the optical actuation beam over the sample so as to bring different parts of the sample into an optical contact with the optical actuation beam.

25. The method of claim 22, wherein the microparticle probes comprise melamine resin beads.

26. The method of claim 22, wherein the microparticle probes are between 1 nanometer and 10 micrometers in diameter.

* * * * *